US012655093B2

(12) United States Patent
Kantzer et al.

(10) Patent No.: US 12,655,093 B2
(45) Date of Patent: Jun. 16, 2026

(54) MANUFACTURE OF NITRILE COMPOUNDS

(71) Applicant: NOURYON CHEMICALS INTERNATIONAL B.V., Amsterdam (NL)

(72) Inventors: Eike Nicolas Kantzer, Uddevalla (SE); Alexey Borisovich Zaitsev, Deventer (NL); Tjerk Oedse Boonstra, Duiven (NL); Ina Ehlers, Stenungsund (SE); Rolf Krister Edvinsson, Partille (SE); Martin Heus, Arnhem (NL); Antoon Jacob Berend Ten Kate, Arnhem (NL); Michiel Jozef Thomas Raaijmakers, Deventer (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 432 days.

(21) Appl. No.: 18/257,595

(22) PCT Filed: Dec. 14, 2021

(86) PCT No.: PCT/EP2021/085649

§ 371 (c)(1),
(2) Date: Jun. 15, 2023

(87) PCT Pub. No.: WO2022/129020

PCT Pub. Date: Jun. 23, 2022

(65) Prior Publication Data

US 2024/0132444 A1 Apr. 25, 2024

(30) Foreign Application Priority Data

Dec. 16, 2020 (EP) .................................... 20214773

(51) Int. Cl.

| | |
|---|---|
| ***C07C 253/30*** | (2006.01) |
| ***C07C 253/12*** | (2006.01) |
| ***C07C 253/34*** | (2006.01) |
| ***C07D 233/02*** | (2006.01) |

(52) U.S. Cl.

CPC .......... *C07C 253/30* (2013.01); *C07C 253/12* (2013.01); *C07C 253/34* (2013.01); *C07D 233/02* (2013.01)

(58) Field of Classification Search

CPC ... C07C 253/30; C07C 253/12; C07C 253/34; C07D 233/02

See application file for complete search history.

(56) References Cited

U.S. PATENT DOCUMENTS

| | | | |
|---|---|---|---|
| 2,785,176 | A | 3/1957 | Vebra |
| 5,399,706 | A | 3/1995 | Dochniak |
| 5,428,156 | A | 6/1995 | Mease et al. |
| 2010/0121064 | A1 * | 5/2010 | Dahmen et al. |
| 2013/0303526 | A1 | 11/2013 | Ni et al. |
| 2015/0065679 | A1 | 3/2015 | Gillet et al. |

FOREIGN PATENT DOCUMENTS

| | | | |
|---|---|---|---|
| EP | 0078169 | A2 | 5/1983 |
| GB | 972003 | A | 10/1964 |
| JP | S58175473 | A | 10/1983 |
| JP | H08508246 | A | 9/1996 |
| JP | 2010520170 | A | 6/2010 |
| JP | 2013538227 | A | 10/2013 |
| JP | 2015512465 | A | 4/2015 |
| WO | 9420474 | A1 | 9/1994 |
| WO | 2020161146 | A1 | 8/2020 |

OTHER PUBLICATIONS

Dhainaut, Alain et al, New Triazine Derivatives as Potent Modulators of Multidrug Resistance, Journal of Medicinal Chemistry, Jan. 21, 1992, p. 2481-96, vol. 35, No. 13, Surenes, France.

* cited by examiner

*Primary Examiner* — Brandon J Fetterolf
(74) *Attorney, Agent, or Firm* — Ingrassia, Fisher & Lorenz, LLP

(57) ABSTRACT

A process for manufacturing a nitrile compound through chain elongation of an alkylene amine compound containing three or more amine units in which at least two amine units are protected by a cyclic urea unit and at least one amine unit is not protected, includes reacting the at least one amine unit that is not protected with glycolonitrile or with the combination of formaldehyde and a cyanide compound selected from HCN and inorganic cyanide salts, to add at least one acetonitrile group to the at least one amine unit that is not protected.

19 Claims, No Drawings

MANUFACTURE OF NITRILE COMPOUNDS

CROSS-REFERENCE TO RELATED APPLICATION

This application is a U.S. National-Stage entry under 35 U.S.C. § 371 based on International Application No. PCT/EP2021/085649, filed Dec. 14, 2021, which was published under PCT Article 21(2) and which claims priority to European Application No. 20214773.2, filed Dec. 16, 2020, which are all hereby incorporated in their entirety by reference.

TECHNICAL FIELD

The present disclosure relates to a process to manufacture nitrile compounds by selective chain elongation of alkylene amine compounds having three or more amine units.

BACKGROUND

Manufacture of nitrile compounds through chain elongation of alkyleneamine compounds is known in the art. It can, e.g., be carried out by reacting the alkyleneamine with glycolonitrile or with the combination of hydrogen cyanide and formaldehyde, to form a chain-elongated nitrile compound. Upon hydrogenation of the nitrile compound an amine compound will be formed. Such a process is for example disclosed in US2010/0121064 for the reaction of EDA with glycolonitrile (called FACH in this state of the art document). However, as is indicated in this reference, the process gives undesired secondary components.

The quantity of secondary components increases with the quantity of amine moieties present in the amine molecules. Hence the quantity of secondary components will become even larger when starting from bigger molecules that contain more amine units than the ones disclosed in US2010/0121064.

It should be noted that chain elongating alkylene amines in which part of the amines are protected with a cyclic urea group is not unknown. Such a process is for example disclosed in US2015/0065679, EP 078169, U.S. Pat. Nos. 5,399,706, 2,785,176, GB 972,003. The processes in these documents are either based on a Michael addition reaction of an amine compound with a material with an activated double bond, such as acrylonitrile, or butenenitrile, or the reaction with an epoxide or a chloride, such as 2-chloroethylamine.

Except for the reaction with 2-chloroethylamine which results in the formation of salt, the Michael addition reactions result in molecules in which no ethylene amine chain elongation finds place. More specifically, the reaction results in either the incorporation of propylene or bigger alkylene chains, or compounds that terminate with an alkyl unit are obtained. The reaction with epoxides will also introduce additional hydroxy groups.

In addition, other objects, desirable features and characteristics will become apparent from the subsequent summary and detailed description, and the appended claims, taken in conjunction with this background.

BRIEF SUMMARY

This disclosure provides a process for manufacturing a nitrile compound through chain elongation of an alkylene amine compound comprising three or more amine units in which at least two amine units are protected by a cyclic urea unit and at least one amine unit is not protected, by reacting the at least one amine unit that is not protected with glycolonitrile or with the combination of formaldehyde and a cyanide compound chosen from HCN and inorganic cyanide salts, to add at least one acetonitrile group to the at least one amine unit that is not protected.

DETAILED DESCRIPTION

The following detailed description is merely exemplary in nature and is not intended to limit the present disclosure or the application and uses of the present disclosure. Furthermore, there is no intention to be bound by any theory presented in the preceding background of the present disclosure or the following detailed description.

In this disclosure, the terminology "about" can describe values ±0.1, 0.5, 1, 2, 3, 4, 5, 6, 7, 8, 9, or 10%, in various embodiments. Moreover, it is contemplated that, in various non-limiting embodiments, it is to be appreciated that all numerical values as provided herein, save for the actual examples, are approximate values with endpoints or particular values intended to be read as "about" or "approximately" the value as recited. It is also contemplated that all isomers and chiral options for each compound described herein are hereby expressly contemplated for use herein in various non-limiting embodiments.

Surprisingly it has been found that in the process of the present disclosure acetonitrile chains are selectively added to the amine group or groups in an alkylene amine compound that are not part of a cyclic urea unit, without the formation of salt and without introducing additional functional groups.

As an additional advantage of the process of the present disclosure is that, due to the presence of the cyclic urea unit that makes the amine units unavailable for reacting with one another, in many embodiments cyclization or polymerization reactions which can take place when hydrogenating an acetonitrile terminal compound, such as e.g. when hydrogenating ethylenediamino acetonitrile, can be prevented. Also, due to the presence of the urea group there are fewer amino groups present. In consequence, there will be fewer side reactions where a nitrile group reacts with another amino group, resulting in the formation of fewer side products and thereby increasing selectivity. In addition, other objects, desirable features and characteristics will become apparent from the subsequent summary and detailed description, and the appended claims, taken in conjunction with this background. It is to be appreciated that all numerical values as provided herein, save for the actual examples, are approximate values with endpoints or particular values intended to be read as "about" or "approximately" the value as recited.

It has now been found that it is possible to protect primary and secondary amine groups in an alkylene amine compound containing three or more amine units with a cyclic urea unit and to selectively react the alkylene amine on the amine groups that are not part of such a cyclic urea unit with glycolonitrile or with the combination of formaldehyde and a cyanide compound selected from HCN and inorganic cyanide salts. This will make for the formation of less side products.

Accordingly, the present disclosure provides a process for manufacturing nitrile compounds through chain elongation of an alkylene amine compound containing three or more amine units in which at least two amine units are protected by a cyclic urea unit and at least one amine unit is not protected, by reacting the at least one amine unit that is not protected with glycolonitrile or with the combination of formaldehyde and a cyanide compound selected from HCN and inorganic cyanide salts, to add at least one acetonitrile group to the at least one amine unit that is not protected.

As the process of the present disclosure allows the manufacture of nitrile compounds in a more selective manner, it is possible to apply more stringent reaction conditions which lead to a higher conversion, allowing the production of the desired nitrile compounds in high yield.

Furthermore it has been found that when using glycolonitrile as the reactant it is possible to selectively add one acetonitrile unit to the not protected amine group. It has also been found that when employing a cyanide compound and formaldehyde it is possible to selectively add two acetonitrile units to the amine group or groups that are not part of the cyclic urea unit.

Accordingly, the process of the present disclosure provides many options for preparing selectively chain elongated alkylene amines. As a consequence of the selective reaction, less effort is required to separate the reaction mixture, resulting in a reduction in both processing and apparatus cost.

The process of the present disclosure results in the formation of a compound comprising at least one acetonitrile group and at least two amine units protected by a cyclic urea unit. This compound can be further processed as desired, as will be discussed below.

The process as contemplated herein will be discussed in more detail below.

The starting compound in the process as contemplated herein is an alkylene amine compound containing three or more amine units in which at least two amine units are protected by a cyclic urea unit and at least one amine unit is not protected.

The wording two amine units protected by a cyclic urea unit refers to a unit of formula I.

Formula I

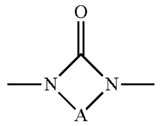

wherein A is selected from the group of C2 to C4 alkylene units, optionally substituted by one or more C1 to C3 alkyl groups. In the cyclic alkyleneurea group, it is preferred for A to be a C2 to C3 alkylene unit, optionally substituted with one or two C1 alkyl groups. A preferably is selected from the group of ethylene, propylene, and isopropylene, specifically ethylene. Where more than one A is present in a molecule, each A can be selected independently.

In one embodiment, the starting compound is an alkyleneurea compound which comprises at least one primary or secondary amine group and at least one cyclic alkyleneurea group of formula I. It is preferred for the (not protected) amine group to be a primary amine group or a cyclic secondary amine group. It is particularly preferred for the amine group to be a primary amine group.

The alkylene amine compound used as starting material in the present disclosure contains at least one cyclic urea unit of formula I. In general, the alkylene amine compound will contain at most 10 cyclic urea units of formula I. In practice, the alkylene amine compound will often contain at most 5 cyclic urea units of formula I. The alkylene amine compound contains at least one amine unit that is not protected. In general, the alkylene amine compound will contain at most 5 not protected amine units. In practice, the alkylene amine compound will often contain at most three not protected amine units, in particular one or two, specifically one.

The alkylene units in the alkyleneamine compound generally have one to 10 carbon atoms, in particular 1 to 8. In one embodiment, the alkylene units meet the requirements for A described above.

In one embodiment, the alkylene amine compound does not comprise further moieties than amine units and alkylene units.

In another embodiment, the alkylene amine compound does comprise further moieties than amine units and alkylene units. Such moieties may, e.g., be selected from C1-C6 alkyl groups which are optionally substituted with —OH, —COOH, and/or COO-alkyl, and ether moieties (—O—).

The alkylene amine compound generally has a molecular weight in the range of 115 to 10.000 g/mol, in particular 115 to 1000 g/mol, in some embodiments 115-500 g/mol.

In one embodiment, the alkyleneurea compound is a compound of formula II:

R2-[—X—A-]$_q$—N(A)(CO)N—[A-X—]$_p$—A-NH2    Formula II wherein

R2 is selected from H and C1 to C6 alkyl groups which are optionally substituted by one or more groups selected from —OH, —NH2, and —COOR4, in particular zero, one, or two groups selected from —OH, —NH2, and COOR4, in particular zero, one, or two groups selected from —OH and —NH2, wherein R4 is H or C1 to C6 alkyl;

X is on each occurrence independently selected from —O—, —NR2-, groups of Formula I, and groups of Formula III:

Formula I

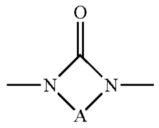

Formula III

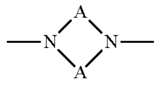

A has the meaning discussed above, wherein where more than one A is present in a molecule, each A can be selected independently, p is an integer in the range of from 0 to 8, and q is an integer in the range of 0 to 8.

For the avoidance of doubt, the structure —N(A)(CO)N— in formula II corresponds to Formula I.

The preferences for A given above also apply here. It is particularly preferred for A to be ethylene.

It is preferred for X to be selected from —NH—, groups of Formula III, and groups of Formula I. Where it is desired to manufacture straight-chain alkyleneamines, it is preferred for X to be selected from NH and groups of formula I.

It is preferred for R2 to be selected from H, ethyl, propyl, and isopropyl, in particular ethyl, optionally substituted by one or two groups selected from —OH and —NH2. It is particularly preferred for R2 to be ethyl, or propyl, in particular ethyl, substituted with —NH2 at the second carbon atom (aminoethyl or aminoisopropyl) or, in the case of propyl, at the third carbon atom, counted from the connection to X.

As the reaction of large molecules to form even larger molecules is not always aimed for, it may be preferred for the total of p and q to be at most 8, in some embodiments at most 4, or at most 2.

Examples of preferred compounds of Formula II are the urea adduct of diethylene triamine (U-DETA), the monourea adduct of triethylene tetramine, wherein the urea group may be at the terminal ethylene moiety or at the central ethylene moiety (U1-TETA and U2-TETA), and the mono- and di-urea adducts of tetraethylenepentamine with a primary amine group (U1-TEPA, DU1,3-TEPA). These compounds are particularly attractive if it is desired to produce nitrile compounds of linear polyethyleneamines and their respective urea products.

Examples of other compounds which may be used in one embodiment of the process as contemplated herein are compounds consisting of or including an ethylene amine chain provided with a urea group over the nitrogen atoms on each side of the terminal ethylene moiety and with an ethylene chain over the nitrogen atoms on each side of another ethylene moiety, e.g., U1P3-TEPA and U1P4-TEPA.

In general in the present specification, the compounds are named as follows. The letter code refers to the longest linear ethyleneamine chain.

A U refers to the presence of a cyclic urea group, resulting from the presence of a urea group over two adjacent nitrogen atoms connected through an ethylene moiety, i.e. a group of formula I wherein A is an ethylene group.

A P refers to the presence of a piperazine moiety resulting from the presence of an ethylene moiety over two adjacent nitrogen atoms connected through an ethylene moiety, i.e. a group of Formula III wherein both As are ethylene groups. Numbers after the U or P prefix refer to the respective nitrogen atom in the chain in order to distinguish among different possible structures. Letters preceding the U or P prefix refer to the number of groups, with D standing for di, or two groups, T standing for tri and tetra, or three and four groups, respectively. Where T is used, it will be clear from the context whether tri or tetra is meant.

In another embodiment, the alkyleneurea compound is a compound of formula IV $$\text{R2-[—X—A-]}_q\text{—N(A)(CO)N—[A-X—]}_p\text{—A-N(A)(A)N—[—A-X—]}_r\text{—R3} \quad \text{Formula IV}$$

wherein R2, X, A, q and p have the meanings given above. The preferences given above also apply here.

R3 is selected from H and C1 to C6 alkyl groups which are optionally substituted by one or more groups selected from —OH and —NH2, in particular zero, one, or two groups selected from —OH and —NH2. It is preferred for R3 to be selected from H, ethyl, propyl, and isopropyl, in particular ethyl, optionally substituted by one or two groups selected from —OH and —NH2. It is particularly preferred for R3 to be ethyl, or propyl, in particular ethyl, substituted with —NH2 at the second carbon atom (aminoethyl or aminoisopropyl) or, in the case of propyl, at the third carbon atom, counted from the connection to X.

In formula IV r is an integer between 0 and 8, in particular between 0 and 4, more in particular 0, 1, or 2. As the reaction of large molecules to form even larger molecules is not always aimed for, it may be preferred for the total of p, q, and r to be at most 8, in some embodiments at most 4, or at most 2.

For the avoidance of doubt, the structure —N(A)(CO)N— in formula IV corresponds to Formula I. The structure —N(A)(A)N— in formula IV corresponds to Formula III.

Examples of preferred compounds of formula IV include the urea adduct of piperazinoethylethylenediamine (UP-TETA). U1P3-TEPA and U1P4-TEPA are also preferred.

Mixtures of alkyleneurea compounds may also be employed.

In a preferred embodiment the alkylene amine containing 3 or more amine units in which at least 2 amine units are protected by a cyclic urea unit and at least 1 amine unit is not protected, which is the starting compound in the process of the present disclosure is selected from the group of U-DETA, U1-TETA, UP-TETA, U2-TETA, DU1,3-TEPA, DU1,4-TEPA, U1P3-TEPA, and U1P4-TEPA.

The starting compound as described above is reacted with glycolonitrile or with the combination of formaldehyde and a cyanide compound selected from HCN and inorganic cyanide salts. These reactions will be discussed below.

In one embodiment the starting compound as described above is reacted with glycolonitrile. Glycolonitrile is also known as hydroxyacetonitrile or formaldehyde cyanohydrin. The following is an example of this reaction, with U-DETA being used as starting material. Water (not shown) is also formed in the reaction.

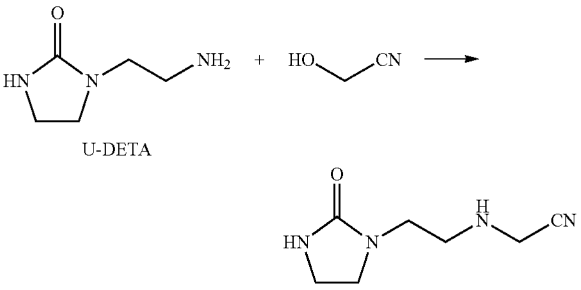
U-DETA

The reaction between the starting compound and glycolonitrile is generally carried out at a temperature of 0-100° C., in particular between 0 and 50° C., more in particular between 0 and 35° C. The reaction is generally carried out at a pressure of 0.5-10 bar. As elevated pressure is not required, it may be attractive to carry out the reaction at a pressure of 0.5-5 bar, in particular 0.5-3 bar. Atmospheric pressure is considered preferred. Where pressures in bar are mentioned in the present specification, bar(a) is meant.

The reaction can take place in a solvent. Water would be a suitable solvent, but other solvents in which the reactants can dissolve under reaction conditions but which do not to a substantial extent react under reaction conditions may also be considered. Other suitable solvents include organic solvents, for example amides such as N-methylpyrrolidone (NMP) and dimethylformamide (DMF), aromatic and aliphatic hydrocarbons such as benzene and xylene, alcohols such as methanol, ethanol, propanol, isopropanol, butanol, isobutanol, secondary butanol and tertiary butanol, amines such as ethylene amines, alkylamines, ammonia, esters such as methyl acetate or ethyl acetate and ethers such as diisopropyl ether, diisobutyl ether, glycol dimethyl ether, diglycol dimethyl ether, dioxane and tetrahydrofuran (THF). The use of ethers, in particular cyclic ethers, more in particular tetrahydrofuran is considered preferred. Alternatively, alcohols, in particular methanol, as organic solvent may be preferred. The use of amines and ammonia, while possible, may be less attractive as they may take part in the reaction.

As will be clear to the skilled person, the reaction can be carried out in a batch process or in a continuous process.

Suitable reactors and process configurations are known in the art and require no elucidation here.

The molar ratio between the starting compound and glycolonitrile will depend on the desired chain elongation and the number of reactive amine groups in the starting compound. In general, the molar ratio of glycolonitrile to reactive amine groups in the starting material is in the range of, 0.25:1 to 4:1. As an excess of glycolonitrile is in principle not required, it is preferred for the molar ratio of glycolonitrile to reactive amine groups in the starting material to be at most 3:1, in particular at most 2:1, more in particular at most 1.5:1.

Where the starting compound contains one reactive amine group, it will generally be desired to obtain full conversion of the reactive amine groups into monocyanomethylated product. In this case it is therefore preferred for the molar ratio of glycolonitrile to reactive amine group (which is the same as the starting compound in this case), to be at least 0.5:1, in particular at least 0.75:1, more in particular at least 0.9:1, in particular at least 1:1.

Where the starting compound contains more than one reactive amine group, the molar ratio of glycolonitrile to primary amine groups in the reaction mixture will depend on the desired extent of chain extension and thus the desired extent of conversion. When it is desired to react all amine groups to obtain full conversion, the values for the molar ratio of glycolonitrile to reactive amine group groups given above apply. When it is desired to convert only part of the amine groups, lower ratios will be applicable. In this case it may be preferred for the molar ratio of glycolonitrile to reactive amine group to be in the range of 0.25:1 to 1:1, in particular in the range of 0.25:1 to 0.9:1, or 0.25:1 to 0.7:1, or 0.25:1 to 0.5:1.

For example, U2-TETA can react with one to two glycolonitrile molecules to form mono- or dicyanomethylated U2-TETA or mixtures thereof. A lower glycolonitrile to amine group ratio will lead to the formation of more mono-cyanomethylated U2-TETA, while a higher glycolonitrile to primary amine group ratio will lead to the formation of more dicyanomethylated U2-TETA.

As the skilled person is aware, there is often a trade-off between conversion of the starting material and selectivity to the desired product, where increased conversion of starting material may be accompanied by increased formation of side products, resulting in a decrease of selectivity to the desired product. Taking this into account it is within the scope of the skilled person to select reaction conditions (reaction time, reaction temperature, . . . ) and the ratios between the reactants in such a way that the desired balance between conversion and selectivity towards the desired product is obtained.

In another embodiment, the starting compound as described above is reacted with the combination of formaldehyde and a cyanide compound selected from HCN and inorganic cyanide salts. The following is an example of this reaction, with U-DETA being used as starting material.

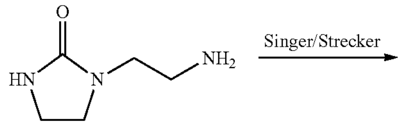

U-DETA

-continued

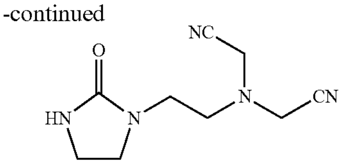

In one embodiment, the cyanide compound is HCN. In this case the reaction is preferably carried out at a temperature in the range of −5° C. to 90° C., in particular in the range of 0° C. to 60° C. and a pressure of 0.5-10 bar. As elevated pressure is not required, it may be attractive to carry out the reaction at a pressure of 0.5-5 bar, in particular 0.5-3 bar. Atmospheric pressure may be preferred.

The reaction can take place in a solvent. Water would be a suitable solvent, but other solvents in which the reactants can dissolve under reaction conditions may also be considered. The solvents mentioned above for the reaction with glycolonitrile may also be applied here.

As will be clear to the skilled person, the reaction can be carried out in a batch process or in a continuous process. Suitable reactors and process configurations are known in the art and require no elucidation here.

The reaction is preferably carried out at a pH in the range of 1 to 9, more in particular 2 to 7. If necessary, pH adjustment agents can be added.

For this process, among other features, the addition of formaldehyde and hydrocyanic acid can be used as a tool to control the balance between selectivity and conversion.

In another embodiment, the cyanide compound is an inorganic cyanide salt. In this case, the cyanide salt is preferably selected from alkaline metal cyanide salts and alkaline earth metal cyanide salts. Suitable alkaline metal salts include salts of sodium, potassium, and lithium, with sodium and potassium being preferred and sodium being particularly preferred. An example of a suitable alkaline earth metal salt is calcium cyanide. In general, it is preferred for the cyanide compound to be soluble in the reaction medium under reaction conditions.

Where a cyanide salt is used, the end product obtained will depend on the pH of the reaction medium. If the reaction is carried out under acidic conditions, the end product will be a nitrile. In this case, the pH is preferably kept in the range of 1 to 7. If so desired, an acid, e.g., a strong inorganic acid, can be added to keep the pH in the desired range. If the reaction is carried out under strongly basic conditions the nitrile formed in the reaction will react further to form a carboxylate salt. Base, in particular a strong inorganic base such as NaOH or KOH, can be added to promote the formation of carboxylate groups. In this case, it may be preferred for the reaction to be carried out at a pH of 10-14.

The reaction of the starting compound with the combination of formaldehyde and an inorganic cyanide salt is preferably carried out at a temperature of 30 to 150° C., in particular 50 to 130° C.

In one embodiment the ammonia produced by hydrolysis of the nitrile groups is preferably distilled off from the reaction mixture simultaneously with reagent dosing. This allows for higher product purity.

The reaction is generally carried out at a pressure of 0.5-10 bar(a). As elevated pressure is not required, it may be attractive to carry out the reaction at a pressure of 0.5-5 bar, in particular 0.5-3 bar. Atmospheric pressure may be preferred.

The reaction can take place in a solvent. Water would be a suitable solvent, but other solvents in which the reactants can dissolve under reaction conditions may also be considered. The solvents mentioned above for the reaction with glycolonitrile may also be applied here.

As will be clear to the skilled person, the reaction can be carried out in a batch process or in a continuous process. Suitable reactors and process configurations are known in the art and require no elucidation here.

The formaldehyde and the cyanide compound may be provided to the reaction mixture simultaneously or sequentially, in a single dose or in a series of doses. They may be provided to the starting material separately, or they may be combined before being reacted with the starting material. Combinations of the various embodiments are also envisaged. Simultaneous addition of the reagents may be preferred.

The molar ratio between formaldehyde and cyanide compound will be in the range of 0.5:1 to 2:1, in particular 0.7:1 to 1.4:1, more in particular 0.9:1 to 1.1:1, e.g., equimolar. The desired ratio between the starting compound and the cyanide compound will depend on the desired chain elongation, the number of reactive amine groups in the starting compound, and whether the reactive amine groups are primary or secondary amines. In general, for full conversion one cyanide molecule is required per NH-bond to be reacted. Thus, in general, the molar ratio of cyanide compound to reactive NH-bond of the reactive amine in the starting material is in the range of 0.25:1 to 4:1. As an excess of cyanide compound is in principle not required, it is preferred for this ratio to be at most 3:1 or at most 2.5:1, or at most 2:1, or at most 1.5:1, specifically at most 1.2:1. As partial conversion is generally not attractive, the molar ratio of cyanide compound to reactive NH-bond of the reactive amine in the starting material is preferably at least 0.5:1, more preferably at least 0.8, more in particular at least 1:1.

The process as contemplated herein results in the formation of acetonitrile-substituted alkyleneamine compounds. Examples of starting materials and the nitrile products that can be obtained therefrom are in the following table.

| amine starting material | nitrile product | structure |
|---|---|---|
| U-DETA | 2-((2-(2-oxoimidazolidin-1-yl)ethyl)amino)acetonitrile | 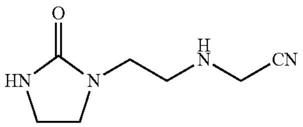 [SMILES: N#CCNCCN1CCNC1=O] |
| U-DETA | 2,2'-((2-(2-oxoimidazolidin-1-yl)ethyl)azanediyl)diacetonitrile | 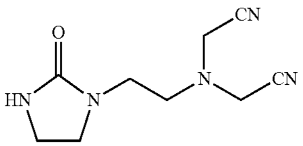 [SMILES: N#CCN(CC#N)CCN1CCNC1=O] |
| U1-TETA | ((2-(2-oxoimidazolidin-1-yl)ethyl)amino)acetonitrile | 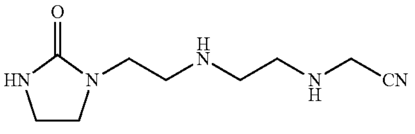 [SMILES: N#CCNCCNCCN1CCNC1=O] |
| U1-TETA | 2-((2-aminoethyl)(2-(2-oxoimidazolidin-1-yl)ethyl)amino)acetonitrile | 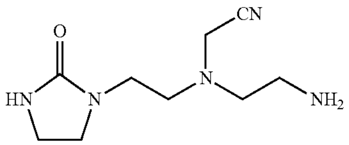 [SMILES: N#CCN(CCN)CCN1CCNC1=O] |
| U1-TETA | 2-((2-((cyanomethyl)(2-(2-oxoimidazolidin-1-yl)ethyl)amino)ethyl)amino)acetonitrile | 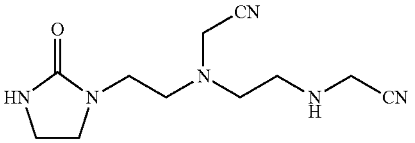 [SMILES: N#CCNCCN(CC#N)CCN1CCNC1=O] |
| U1-TETA | 2,2'-((2-((2-(2-oxoimidazolidin-1-yl)ethyl)amino)ethyl)azanediyl)diacetonitrile | 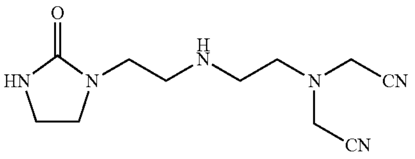 [SMILES: N#CCN(CC#N)CCNCCN1CCNC1=O] |

-continued

| amine starting material | nitrile product | structure |
| --- | --- | --- |
| U1-TETA | 2,2'-((2-((cyanomethyl)(2-(2-oxoimidazolidin-1-yl)ethyl)amino)ethyl)azanediyl)diacetonitrile | 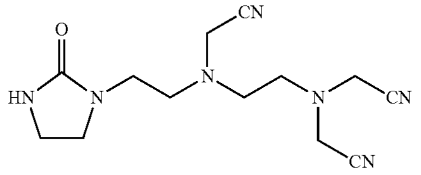 [SMILES: N#CCN(CC#N)CCN(CC#N)CCN1CCNC1=O] |
| U2-TETA | 2-((2-(3-(2-aminoethyl)-2-oxoimidazolidin-1-yl)ethyl)amino)acetonitrile | 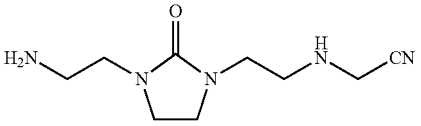 [SMILES: N#CCNCCN1CCN(CCN)C1=O] |
| U2-TETA | 2,2'-(((2-oxoimidazolidine-1,3-diyyl)bis(ethane-2,1-diyl))bis(azanediyl))diacetonitrile | 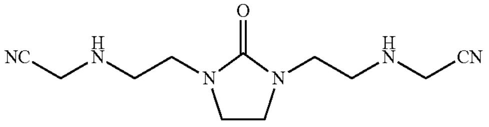 [SMILES: N#CCNCCN1CCN(CCNCC#N)C1=O] |
| U2-TETA | 2,2'-((2-(3-(2-aminoethyl)-2-oxoimidazolidin-1-yl)ethyl)azanediyl)diacetonitrile | 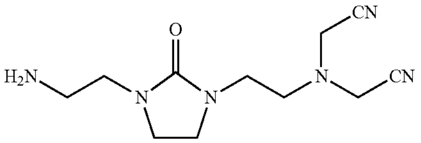 [SMILES: N#CCN(CC#N)CCN1CCN(CCN)C1=O] |
| U2-TETA | 2,2'-((2-(3-(2-((cyanomethyl)amino)ethyl)-2-oxoimidazolidin-1-yl)ethyl)azanediyl)diacetonitrile | 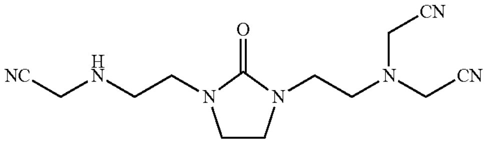 [SMILES: N#CCNCCN1CCN(CCN(CC#N)CC#N)C1=O] |
| U2-TETA | 2,2',2'',2'''-(((2-oxoimidazolidine-1,3-diyl)bis(ethane-2,1-diyl))bis(azanetriyl))tetraacetonitrile | 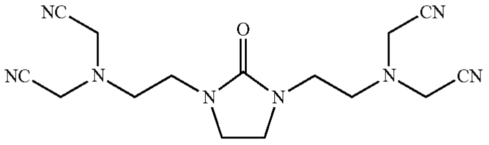 [SMILES: N#CCN(CC#N)CCN1CCN(CCN(CC#N)CC#N)C1=O] |
| UP-TETA | 2-(4-(2-(2-oxoimidazolidin-1-yl)ethyl)piperazin-1-yl)acetonitrile | 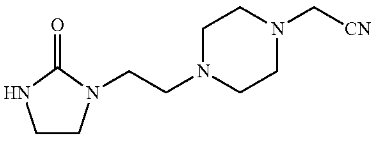 [SMILES: N#CCN1CCN(CCN2CCNC2=O)CC1] |
| DU1,3-TEPA | 2-((2-(2-oxo-3-(2-(2-oxoimidazolidin-1-yl)ethyl)imidazolidin-1-yl)ethyl)amino)acetonitrile | 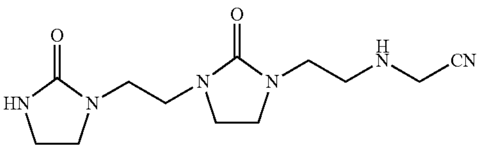 [SMILES: N#CCNCCN1CCN(CCN2CCNC2=O)C1=O] |
| DU1,3-TEPA | 2,2'-((2-(2-oxo-3-(2-(2-oxoimidazolidin-1-yl)ethyl)imidazolidin-1-yl)ethyl)azanediyl)diacetonitrile | 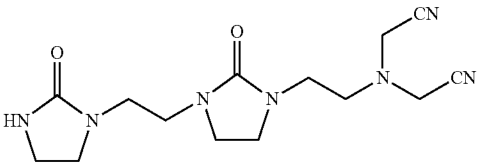 [SMILES: N#CCN(CC#N)CCN1CCN(CCN2CCNC2=O)C1=O] |
| DU1,4-TEPA | 2-(bis(2-(2-oxoimidazolidin-1-yl)ethyl)amino)acetonitrile | 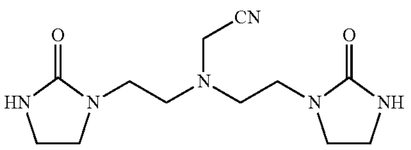 [SMILES: N#CCN(CCN1CCNC1=O)CCN1CCNC1=O] |

-continued

| amine starting material | nitrile product | structure |
|---|---|---|
| U1P3-TEPA | 2-((2-(4-(2-(2-oxoimidazolidin-1-yl)ethyl)piperazin-1-yl)ethyl)amino)acetonitrile | 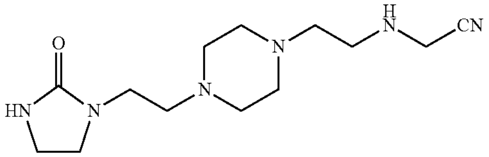 [SMILES: N#CCNCCN1CCN(CCN2CCNC2=O)CC1] |
| U1P3-TEPA | 2,2'-((2-(4-(2-(2-oxoimidazolidin-1-yl)ethyl)piperazin-1-yl)ethyl)azanediyl)diacetonitrile | 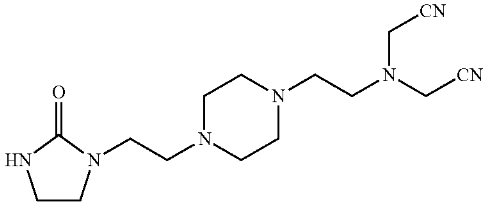 [SMILES: N#CCN(CC#N)CCN1CCN(CCN2CCNC2=O)CC1] |
| U1P4-TEPA | 2-(4-(2-((2-(2-oxoimidazolidin-1-yl)ethyl)amino)ethyl)piperazin-1-yl)acetonitrile | 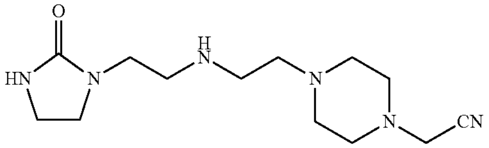 [SMILES: N#CCN1CCN(CCNCCN2CCNC2=O)CC1] |
| U1P4-TEPA | 2-((2-(2-oxoimidazolidin-1-yl)ethyl)(2-(piperazin-1-yl)ethyl)amino)acetonitrile | 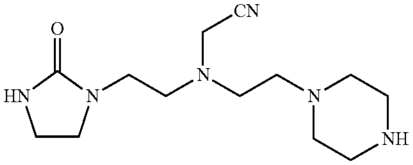 [SMILES: N#CCN(CCN1CCNCC1)CCN1CCNC1=O] |
| U1P4-TEPA | 2-(4-(2-((cyanomethyl)(2-(2-oxoimidazolidin-1-yl)ethyl)amino)ethyl)piperazin-1-yl)acetonitrile | 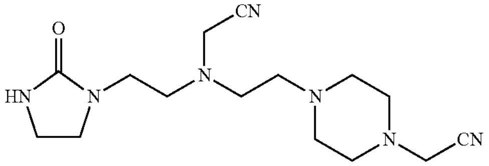 [SMILES: N#CCN1CCN(CCN(CC#N)CCN2CCNC2=O)CC1] |

Other combinations of starting materials and the nitrile products that can be obtained therefrom are in the following table.

| amine starting material | nitrile product | structure |
|---|---|---|
| U2-TEPA | 2-((2-((2-(3-(2-aminoethyl)-2-oxoimidazolidin-1-yl)ethyl)amino)ethyl)amino)acetonitrile | 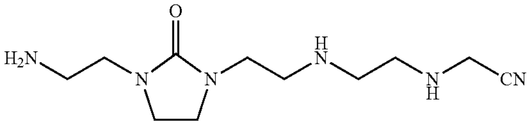 [SMILES: N#CCNCCNCCN1CCN(CCN)C1=O] |
| U2-TEPA | 2-((2-aminoethyl)(2-(3-(2-aminoethyl)-2-oxoimidazolidin-1-yl)ethyl)amino)acetonitrile | 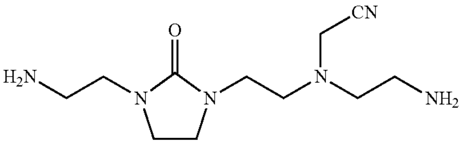 [SMILES: N#CCN(CCN)CCN1CCN(CCN)C1=O] |

-continued

| amine starting materi-al | nitrile product | structure |
|---|---|---|
| U2-TEPA | 2-((2-(3-(2-((2-aminoethyl)amino)ethyl)-2-oxoimidazolidin-1-yl)ethyl)amino)acetonitrile | 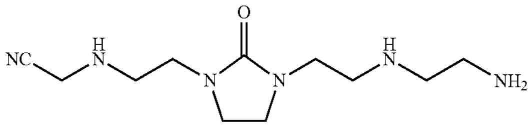 [SMILES: N#CCNCCN1CCN(CCNCCN)C1=O] |
| U2-TEPA | 2-((2-((2-(3-(2-((cyanomethyl)amino)ethyl)-2-oxoimidazolidin-1-yl)ethyl)amino)ethyl)amino)acetonitrile | 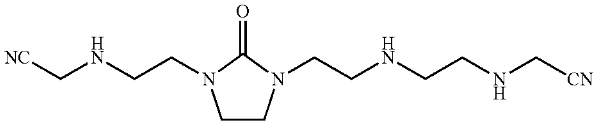 [SMILES: N#CCNCCNCCN1CCN(CCNCC#N)C1=O] |
| U2-TEPA | 2,2'-((2-(3-(2-((2-aminoethyl)amino)ethyl)-2-oxoimidazolidin-1-yl)ethyl)azanediyl)diacetonitrile | 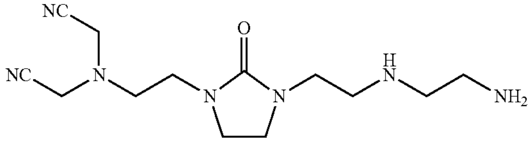 [SMILES: N#CCN(CC#N)CCN1CCN(CCNCCN)C1=O] |
| U2-TEPA | 2-((2-aminoethyl)(2-(3-(2-((cyanomethyl)amino)ethyl)-2-oxoimidazolidin-1-yl)ethyl)amino)acetonitrile | 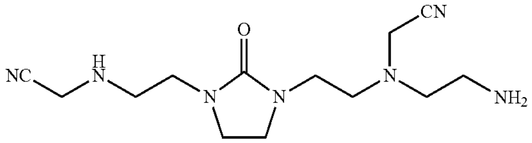 [SMILES: N#CCNCCN1CCN(CCN(CC#N)CCN)C1=O] |
| U2-TEPA | 2,2'-((2-((2-(3-(2-aminoethyl)-2-oxoimidazolidin-1-yl)ethyl)amino)ethyl)azanediyl)diacetonitrile | 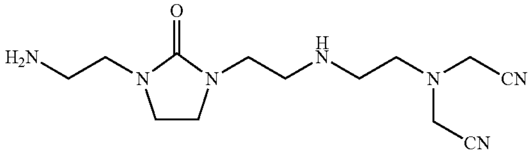 [SMILES: N#CCN(CC#N)CCNCCN1CCN(CCN)C1=O] |
| U2-TEPA | 2-((2-(3-(2-aminoethyl)-2-oxoimidazolidin-1-yl)ethyl)(2-((cyanomethyl)amino)ethyl)amino)acetonitrile | 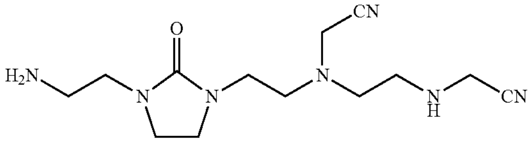 [SMILES: N#CCNCCN(CC#N)CCN1CCN(CCN)C1=O] |
| U2-TEPA | 2,2'-((2-((2-(3-(2-((cyanomethyl)amino)ethyl)-2-oxoimidazolidin-1-yl)ethyl)amino)ethyl)azanediyl)diacetonitrile | 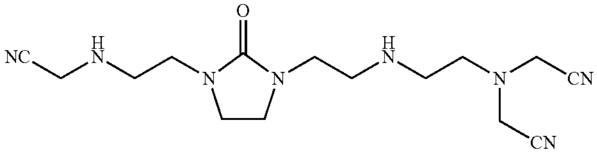 [SMILES: N#CCNCCN1CCN(CCNCCN(CC#N)CC#N)C1=O] |
| U2-TEPA | 2,2'-((2-(3-(2-((2-((cyanomethyl)amino)ethyl)amino)ethyl)-2-oxoimidazolidin-1-yl)ethyl)azanediyl)diacetonitrile | 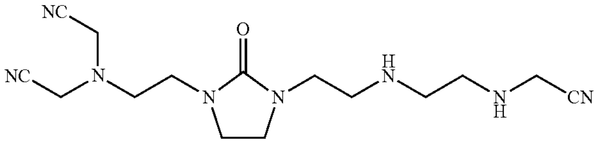 [SMILES: N#CCNCCNCCN1CCN(CCN(CC#N)CC#N)C1=O] |
| U2-TEPA | 2-((2-(3-(2-((cyanomethyl)(2-((cyanomethyl)amino)ethyl)amino)ethyl)-2-oxoimidazolidin-1-yl)ethyl)amino)acetonitrile | 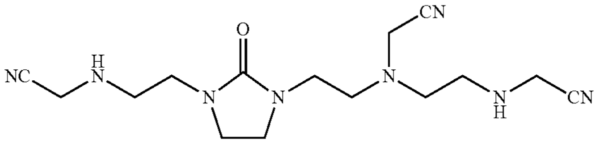 [SMILES: N#CCNCCN(CC#N)CCN1CCN(CCNCC#N)C1=O] |

-continued

| amine starting materi-al | nitrile product | structure |
|---|---|---|
| U2-TEPA | 2,2'-((2-((2-(3-(2-aminoethyl)-2-oxoimidazolidin-1-yl)ethyl)(cyanomethyl)amino)ethyl)azanediyl)diacetonitrile | 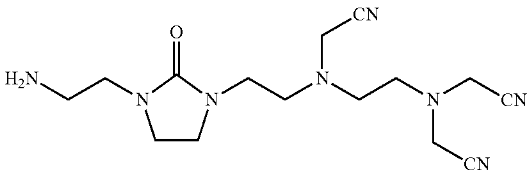 [SMILES: N#CCN(CC#N)CCN(CC#N)CCN1CCN(CCN)C1=O] |
| U2-TEPA | 2,2'-((2-(3-(2-((2-aminoethyl)(cyanomethyl)amino)ethyl)-2-oxoimidazolidin-1-yl)ethyl)azanediyl)diacetonitrile | 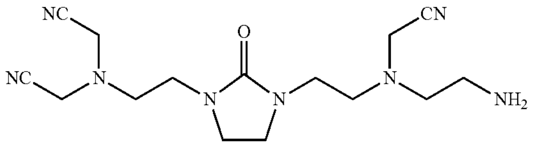 [SMILES: N#CCN(CC#N)CCN1CCN(CCN(CC#N)CCN)C1=O] |
| U2-TEPA | 2,2'-((2-((2-(3-(2-(bis(cyanomethyl)amino)ethyl)-2-oxoimidazolidin-1-yl)ethyl)amino)ethyl)azanediyl)diacetonitrile | 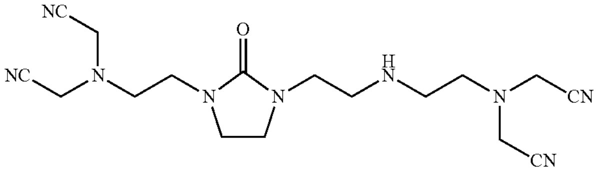 [SMILES: N#CCN(CC#N)CCNCCN1CCN(CCN(CC#N)CC#N)C1=O] |
| U2-TEPA | 2,2'-((2-((cyanomethyl)(2-(3-(2-((cyanomethyl)amino)ethyl)-2-oxoimidazolidin-1-yl)ethyl)amino)ethyl)azanediyl)diacetonitrile | 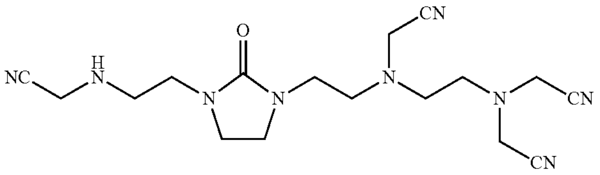 [SMILES: N#CCNCCN1CCN(CCN(CC#N)CCN(CC#N)CC#N)C1=O] |
| U2-TEPA | 2,2'-((2-(3-(2-((cyanomethyl)(2-((cyanomethyl)amino)ethyl)amino)ethyl)-2-oxoimidazolidin-1-yl)ethyl)azanediyl)diacetonitrile | 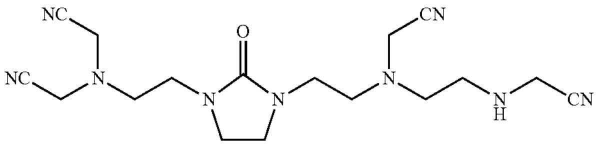 [SMILES: N#CCNCCN(CC#N)CCN1CCN(CCN(CC#N)CC#N)C1=O] |
| U2-TEPA | 2,2'-((2-(3-(2-((2-(bis(cyanomethyl)amino)ethyl)(cyanomethyl)amino)ethyl)-2-oxoimidazolidin-1-yl)ethyl)azanediyl)diacetonitrile | 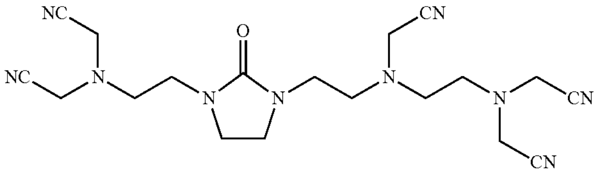 [SMILES: N#CCN(CC#N)CCN(CC#N)CCN1CCN(CCN(CC#N)CC#N)C1=O] |
| U1-T-TEPA | 2-((2-((2-aminoethyl)(2-(2-oxoimidazolidin-1-yl)ethyl)amino)ethyl)amino)acetonitrile | 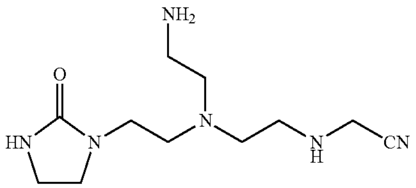 [SMILES: N#CCNCCN(CCN)CCN1CCNC1=O] |
| U1-T-TEPA | 2,2'-((((2-(2-oxoimidazolidin-1-yl)ethyl)azanediyl)bis(ethane-2,1-diyl))bis(azanediyl))diacetonitrile | 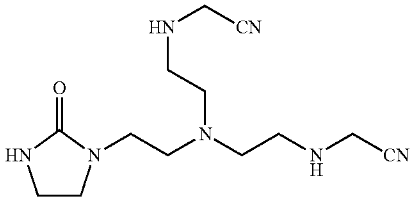 [SMILES: N#CCNCCN(CCNCC#N)CCN1CCNC1=O] |

-continued

| amine starting material | nitrile product | structure |
|---|---|---|
| U1-T-TEPA | 2,2'-((2-((2-aminoethyl)(2-(2-oxoimidazolidin-1-yl)ethyl)amino)ethyl)azanediyl)diacetonitrile | 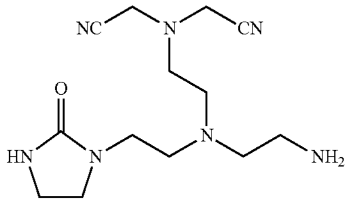 [SMILES: N#CCN(CC#N)CCN(CCN)CCN1CCNC1=O] |
| U1-T-TEPA | 2,2'-((2-((2-aminoethyl)(2-(2-oxoimidazolidin-1-yl)ethyl)amino)ethyl)azanediyl)diacetonitrile | 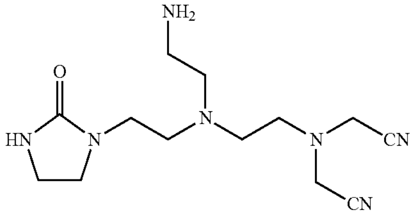 [SMILES: N#CCN(CC#N)CCN(CCN)CCN1CCNC1=O] |
| U1-T-TEPA | 2,2'-((2-((2-((cyanomethyl)amino)ethyl)(2-(2-oxoimidazolidin-1-yl)ethyl)amino)ethyl)azanediyl)diacetonitrile | 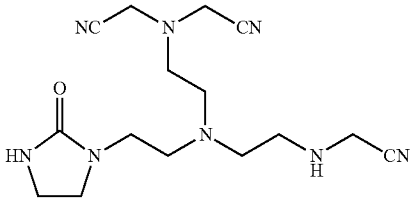 [SMILES: N#CCNCCN(CCN(CC#N)CC#N)CCN1CCNC1=O] |
| U1-T-TEPA | 2,2'-((2-((2-((cyanomethyl)amino)ethyl)(2-(2-oxoimidazolidin-1-yl)ethyl)amino)ethyl)azanediyl)diacetonitrile | 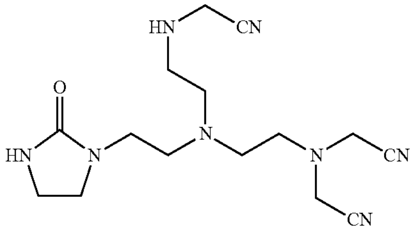 [SMILES: N#CCNCCN(CCN(CC#N)CC#N)CCN1CCNC1=O] |
| U1-T-TEPA | 2,2',2'',2'''-((((2-(2-oxoimidazolidin-1-yl)ethyl)azanediyl)bis(ethane-2,1-diyl))bis(azanetriyl))tetraacetonitrile | 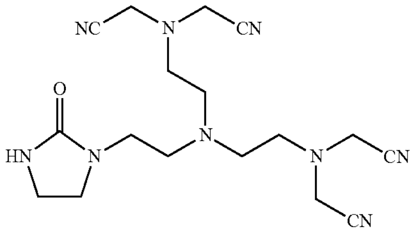 [SMILES: N#CCN(CC#N)CCN(CCN(CC#N)CC#N)CCN1CCNC1=O] |
| U3-PEHA | 2-((2-((2-(3-(2-((2-aminoethyl)amino)ethyl)-2-oxoimidazolidin-1-yl)ethyl)amino)ethyl)amino)acetonitrile | 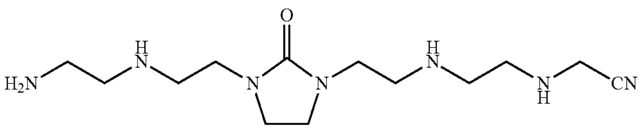 [SMILES: N#CCNCCNCCN1CCN(CCNCCN)C1=O] |
| U3-PEHA | 2-((2-aminoethyl)(2-(3-(2-((2-aminoethyl)amino)ethyl)-2-oxoimidazolidin-1-yl)ethyl)amino)acetonitrile | 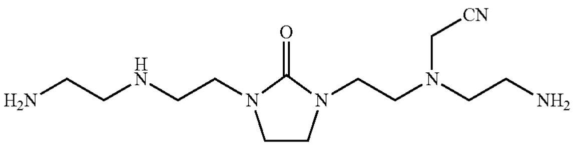 [SMILES: N#CCN(CCN)CCN1CCN(CCNCCN)C1=O] |

-continued

| amine starting materi-al | nitrile product | structure |
|---|---|---|
| U3-PEHA | 2,2'-((((2-oxoimidazolidine-1,3-diyl)bis(ethane-2,1-diyl))bis(azanediyl))bis(eth-ane-2,1-diyl))bis(azanediyl))diace-tonitrile | 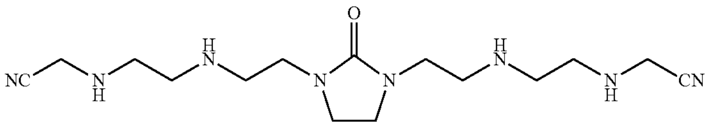 [SMILES: N#CCNCCNCCN1CCN(CCNCCNCC#N)C1=O] |
| U3-PEHA | 2,2'-((2-((2-(3-(2-((2-aminoethyl)amino)ethyl)-2-oxoimidazolidin-1-yl)ethyl)amino)ethyl)azane-diyl)diacetonitrile | 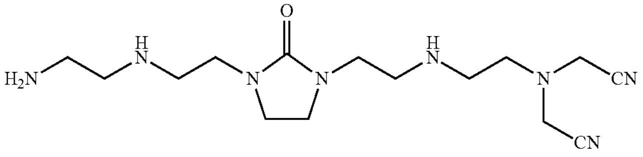 [SMILES: N#CCN(CC#N)CCNCCN1CCN(CCNCCN)C1=O] |
| U3-PEHA | 2-((2-(3-(2-((2-aminoethyl)amino)ethyl)-2-oxoimidazolidin-1-yl)ethyl)(2-((cyanomethyl)amino)eth-yl)amino)acetonitrile | 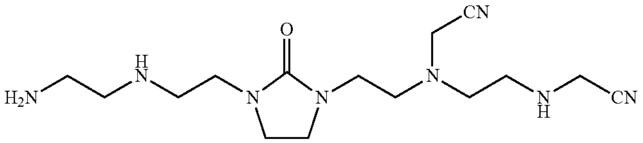 [SMILES: N#CCNCCN(CC#N)CCN1CCN(CCNCCN)C1=O] |
| U3-PEHA | 2-((2-aminoethyl)(2-(3-(2-((2-((cyanomethyl)amino)eth-yl)amino)ethyl)-2-oxoimidazolidin-1-yl)ethyl)amino)acetonitrile | 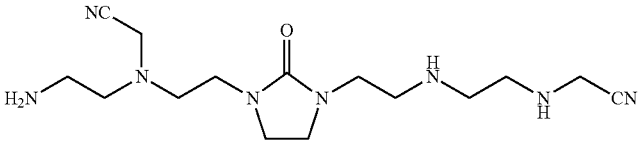 [SMILES: N#CCNCCNCCN1CCN(CCN(CC#N)CCN)C1=O] |
| U3-PEHA | 2,2'-((2-((2-(3-(2-((2-((cyanomethyl)amino)eth-yl)amino)ethyl)-2-oxoimidazolidin-1-yl)ethyl)amino)ethyl)azane-diyl)diacetonitrile | 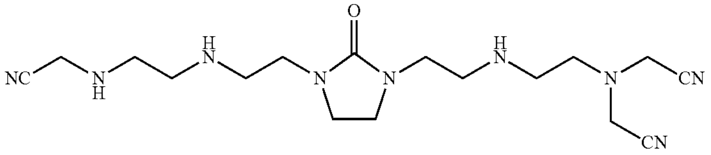 [SMILES: N#CCNCCNCCN1CCN(CCNCCN(CC#N)CC#N)C1=O] |
| U3-PEHA | 2-((2-((2-(3-(2-((cyanomethyl)(2-((cyanomethyl)amino)eth-yl)amino)ethyl)-2-oxoimidazolidin-1-yl)ethyl)amino)ethyl)ami-no)acetonnitrile | 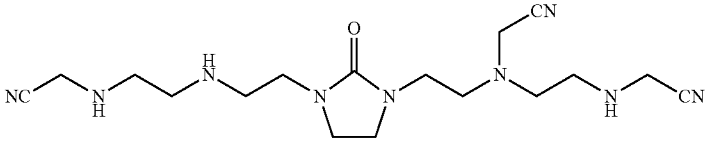 [SMILES: N#CCNCCNCCN1CCN(CCN(CC#N)CCNCC#N)C1=O] |
| U3-PEHA | 2,2'-((2-((2-(3-(2-((2-aminoethyl)amino)ethyl)-2-oxoimidazolidin-1-yl)ethyl)(cyanomethyl)ami-no)ethyl)azanediyl)diaceto-nitrile | 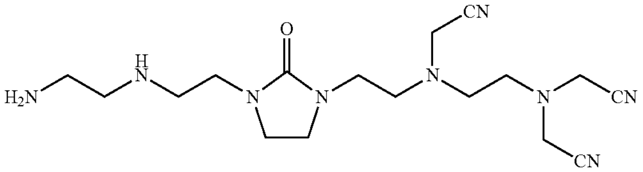 [SMILES: N#CCN(CC#N)CCN(CC#N)CCN1CCN(CCNCCN)C1=O] |
| U3-PEHA | 2,2'-((2-((2-(3-(2-((2-aminoethyl)(cyanomethyl) amino)ethyl)-2-oxoimidazolidin-1-yl)ethyl)amino)ethyl)azane-diyl)diacetonitrile | 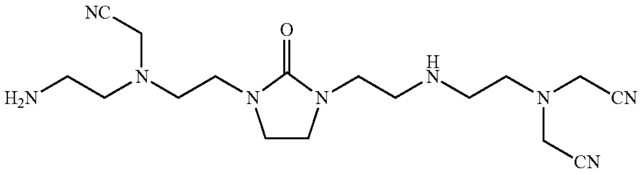 [SMILES: N#CCN(CC#N)CCNCCN1CCN(CCN(CC#N)CCN)C1=O] |
| U3-PEHA | 2,2',2'',2'''-(((((2-oxoimidazolidine-1,3-diyl)bis(ethane-2,1-diyl))bis(azanediyl))bis(eth-ane-2,1-diyl))bis(azanetriyl))tetraa-cetonitrile | 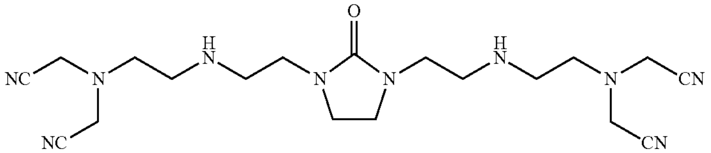 [SMILES: N#CCN(CC#N)CCNCCN1CCN(CCNCCN(CC#N)CC#N)C1=O] |

-continued

| amine starting material | nitrile product | structure |
|---|---|---|
| U3-PEHA | 2,2'-((2-((2-(3-(2-((cyanomethyl)(2-((cyanomethyl)amino)ethyl)amino)ethyl)-2-oxoimidazolidin-1-yl)ethyl)amino)ethyl)azanediyl)diacetonitrile | 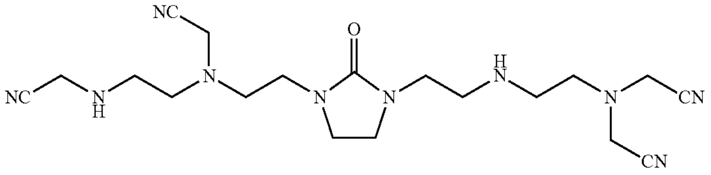 [SMILES: N#CCNCCN(CC#N)CCN1CCN(CCNCCN(CC#N)CC#N)C1=O] |
| U3-PEHA | 2,2'-((2-((cyanomethyl)(2-(3-(2-((2-((cyanomethyl)amino)ethyl)amino)ethyl)-2-oxoimidazolidin-1-yl)ethyl)amino)ethyl)azanediyl)diacetonitrile | 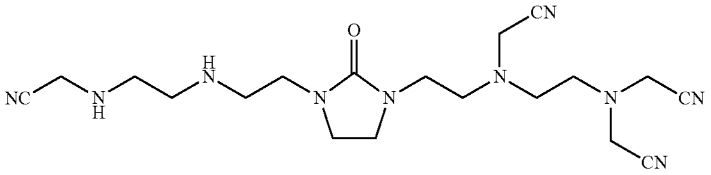 [SMILES: N#CCNCCNCCN1CCN(CCN(CC#N)CCN(CC#N)CC#N)C1=O] |
| U3-PEHA | 2,2'-((2-((2-(3-(2-((2-aminoethyl)(cyanomethyl)amino)ethyl)-2-oxoimidazolidin-1-yl)ethyl)(cyanomethyl)amino)ethyl)azanediyl)diacetonitrile | 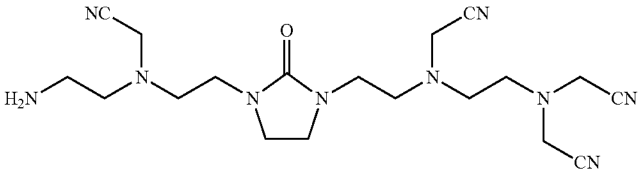 [SMILES: N#CCN(CC#N)CCN(CC#N)CCN1CCN(CCN(CC#N)CCN)C1=O] |
| U3-PEHA | 2,2'-((2-((2-(3-(2-((2-(bis(cyanomethyl)amino)ethyl)(cyanomethyl)amino)ethyl)-2-oxoimidazolidin-1-yl)ethyl)amino)ethyl)azanediyl)diacetonitrile | 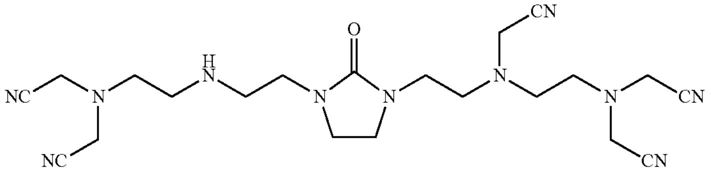 [SMILES: N#CCN(CC#N)CCNCCN1CCN(CCN(CC#N)CCN(CC#N)CC#N)C1=O] |
| U3-PEHA | 2,2'-((2-((cyanomethyl)(2-(3-(2-((cyanomethyl)(2-((cyanomethyl)amino)ethyl)amino)ethyl)-2-oxoimidazolidin-1-yl)ethyl)amino)ethyl)azanediyl)diacetonitrile | 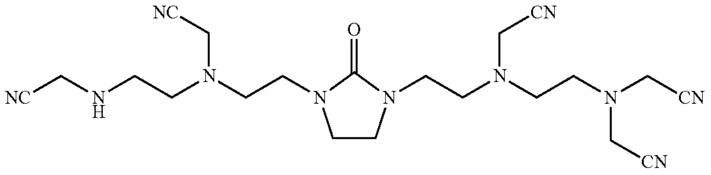 [SMILES: N#CCNCCN(CC#N)CCN1CCN(CCN(CC#N)CCN(CC#N)CC#N)C1=O] |
| U3-PEHA | 2,2',2'',2'''-(((((2-oxoimidazolidine-1,3-diyl)bis(ethane-2,1-diyl))bis((cyanomethyl)azanediyl))bis(ethane-2,1-diyl))bis(azanetriyl))tetraacetonitrile | 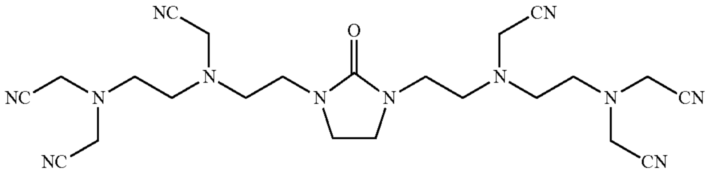 [SMILES: N#CCN(CC#N)CCN(CC#N)CCN1CCN(CCN(CC#N)CCN(CC#N)CC#N)C1=O] |
| U2-T-PEHA | 2-((2-((2-aminoethyl)(2-3-(2-(aminoethyl)-2-oxoimidazolidin-1-yl)ethyl)amino)ethyl)amino)acetonitrile | 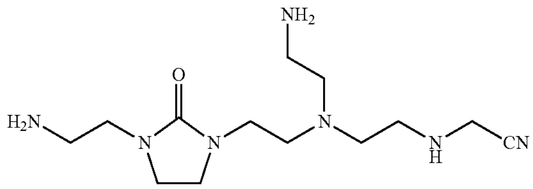 [SMILES: N#CCNCCN(CCN)CCN1CCN(CCN)C1=O] |
| U2-T-PEHA | 2-((2-(3-(2-(bis(2-aminoethyl)amino)ethyl)-2-oxoimidazolidin-1-yl)ethyl)amino)acetonitrile | 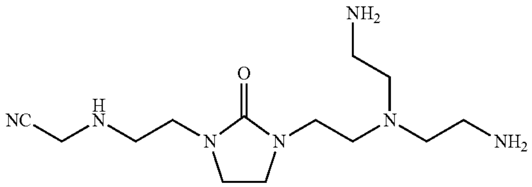 [SMILES: N#CCNCCN1CCN(CCN(CCN)CCN)C1=O] |

-continued

| amine starting materi-al | nitrile product | structure |
|---|---|---|
| U2-T-PEHA | 2-((2-(3-(2-((2-aminoethyl)(2-((cyanomethyl)amino)eth-yl)amino)ethyl)-2-oxoimidazolidin-1-yl)ethyl)amino)acetonitrile | 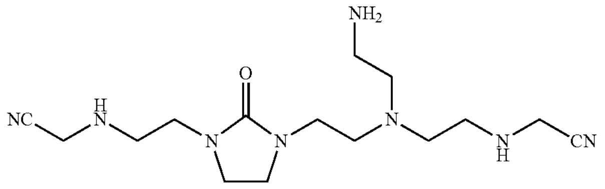 [SMILES: N#CCNCCN(CCN)CCN1CCN(CCNCC#N)C1=O] |
| U2-T-PEHA | 2,2'-((((2-(3-(2-aminoethyl)-2-oxoimidazolidin-1-yl)ethyl)azanediyl)bis(eth-ane-2,1-diyl))bis(azanediyl))diace-tonitrile | 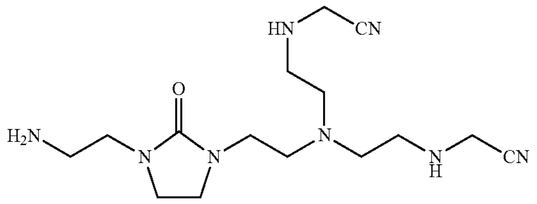 [SMILES: N#CCNCCN(CCNCC#N)CCN1CCN(CCN)C1=O] |
| U2-T-PEHA | 2-((2-(3-(2-((2-aminoethyl)(2-((cyanomethyl)amino)eth-yl)amino)ethyl)-2-oxoimidazolidin-1-yl)ethyl)amino)acetonitrile | 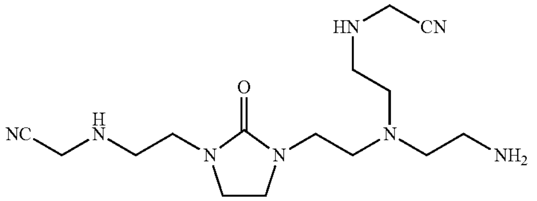 [SMILES: N#CCNCCN(CCN)CCN1CCN(CCNCC#N)C1=O] |
| U2-T-PEHA | 2,2'-((2-((2-aminoethyl)(2-(3-(2-aminoethyl)-2-oxoimidazolidin-1-yl)ethyl)amino)ethyl)azane-diyl)diacetonitrile | 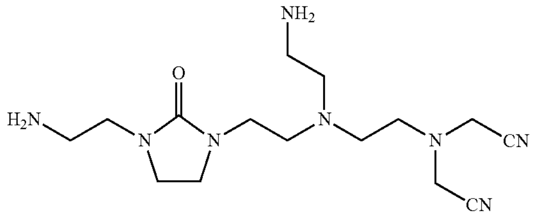 [SMILES: N#CCN(CC#N)CCN(CCN)CCN1CCN(CCN)C1=O] |
| U2-T-PEHA | 2,2'-((2-(3-(2-(bis(2-aminoethyl)amino)ethyl)-2-oxoimidazolidin-1-yl)ethyl)azanediyl)diaceto-nitrile | 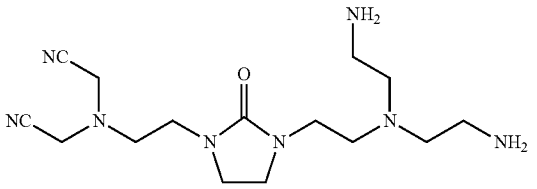 [SMILES: N#CCN(CC#N)CCN1CCN(CCN(CCN)CCN)C1=O] |
| U2-T-PEHA | 2,2'-((((2-(3-(2-((cyanomethyl)amino)eth-yl)-2-oxoimidazolidin-1-yl)ethyl)azanediyl)bis(eth-ane-2,1-diyl))bis(azanediyl))diace-tonitrile | 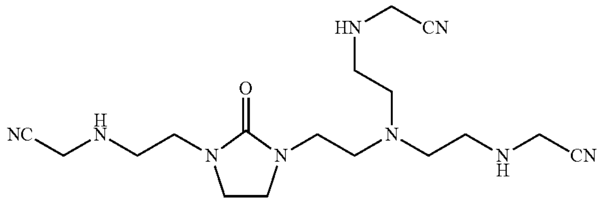 [SMILES: N#CCNCCN(CCNCC#N)CCN1CCN(CCNCC#N)C1=O] |
| U2-T-PEHA | 2,2'-((2-((2-(3-(2-aminoethyl)-2-oxoimidazolidin-1-yl)ethyl)(2-((cyanomethyl)amino)eth-yl)amino)ethyl)azanediyl) diacetonitrile | 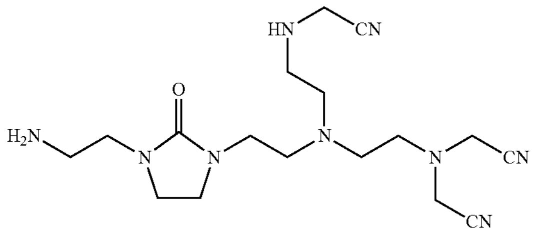 [SMILES: N#CCNCCN(CCN(CC#N)CC#N)CCN1CCN(CCN)C1=O] |

-continued

| amine starting material | nitrile product | structure |
|---|---|---|
| U2-T-PEHA | 2,2'-((2-(3-(2-((2-aminoethyl)(2-((cyanomethyl)amino)ethyl)amino)ethyl)-2-oxoimidazolidin-1-yl)ethyl)azanediyl)diacetonitrile | 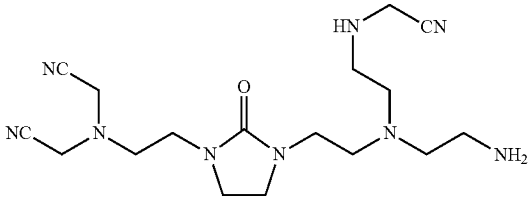 [SMILES: N#CCNCCN(CCN)CCN1CCN(CCN(CC#N)CC#N)C1=O] |
| U2-T-PEHA | 2,2'-((2-((2-aminoethyl)(2-(3-(2-((cyanomethyl)amino)ethyl)-2-oxoimidazolidin-1-yl)ethyl)amino)ethyl)azanediyl)diacetonitrile | 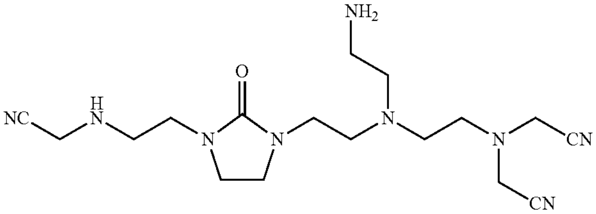 [SMILES: N#CCNCCN1CCN(CCN(CCN)CCN(CC#N)CC#N)C1=O] |
| U2-T-PEHA | 2,2'-((2-((2-((cyanomethyl)amino)ethyl)(2-(3-(2-((cyanomethyl)amino)ethyl)-2-oxoimidazolidin-1-yl)ethyl)amino)ethyl)azanediyl)diacetonitrile | 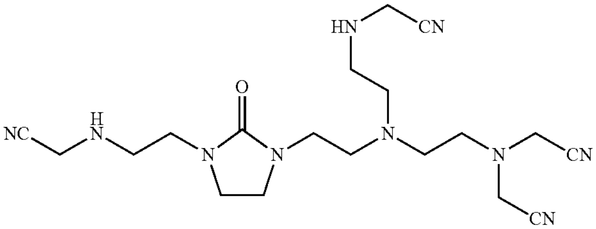 [SMILES: N#CCNCCN(CCN(CC#N)CC#N)CCN1CCN(CCNCC#N)C1=O] |
| U2-T-PEHA | 2,2'-((2-(3-(2-(bis(2-((cyanomethyl)amino)ethyl)amino)ethyl)-2-oxoimidazolidin-1-yl)ethyl)azanediyl)diacetonitrile | 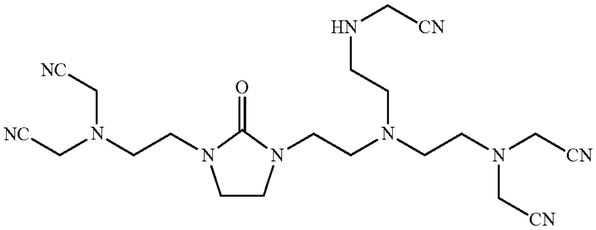 [SMILES: N#CCNCCN(CCN(CC#N)CC#N)CCN1CCN(CCN(CC#N)CC#N)C1=O] |
| U2-T-PEHA | 2,2'-((2-(3-(2-((2-(bis(cyanomethyl)amino)ethyl)(2-((cyanomethyl)amino)ethyl)amino)ethyl)-2-oxoimidazolidin-1-yl)ethyl)azanediyl)diacetonitrile | 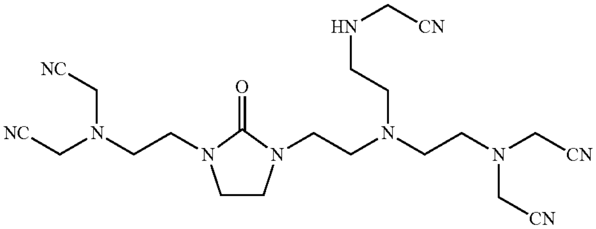 [SMILES: N#CCNCCN(CCN(CC#N)CC#N)CCN1CCN(CCN(CC#N)CC#N)C1=O] |
| U2-T-PEHA | 2,2',2'',2'''-((((2-(3-(2-((cyanomethyl)amino)ethyl)-2-oxoimidazolidin-1-yl)ethyl)azanediyl)bis(ethane-2,1-diyl))bis(azanetriyl))tetraacetonitrile | 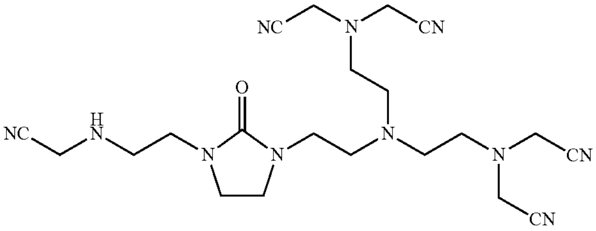 [SMILES: N#CCNCCN1CCN(CCN(CCN(CC#N)CC#N)CCN(CC#N)CC#N)C1=O] |

-continued

| amine starting material | nitrile product | structure |
|---|---|---|
| U2-T-PEHA | 2,2',2'',2'''-((((2-(3-(2-(bis(cyanomethyl)amino)ethyl)-2-oxoimidazolidin-1-yl)ethyl)azanediyl)bis(ethane-2,1-diyl))bis(azanetriyl))tetraacetonitrile | 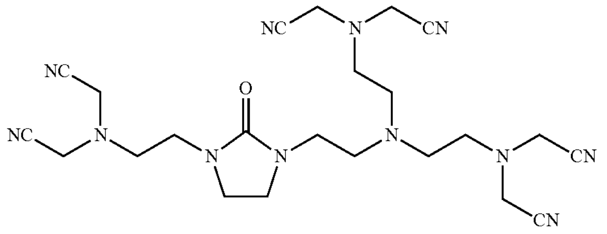 [SMILES: N#CCN(CC#N)CCN(CCN(CC#N)CC#N)CCN1CCN(CCN(CC#N)CC#N)C1=O] |
| U3-T-HEHA | 2-((2-((2-aminoethyl)(2-(3-(2-((2-aminoethyl)amino)ethyl)-2-oxoimidazolidin-1-yl)ethyl)amino)ethyl)amino)acetonitrile | 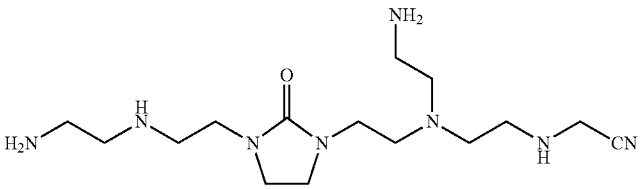 [SMILES: N#CCNCCN(CCN)CCN1CCN(CCNCCN)C1=O] |
| U3-T-HEHA | 2-((2-((2-(3-(2-(bis(2-aminoethyl)amino)ethyl)-2-oxoimidazolidin-1-yl)ethyl)amino)ethyl)amino)acetonitrile | 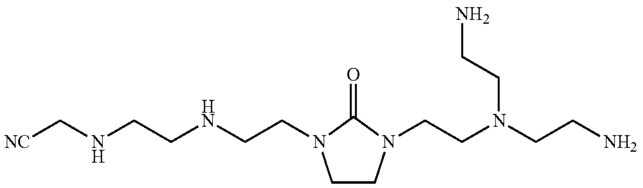 [SMILES: N#CCNCCNCCN1CCN(CCN(CCN)CCN)C1=O] |
| U3-T-HEHA | 2-((2-aminoethyl)(2-(3-(2-(bis(2-aminoethyl)amino)ethyl)-2-oxoimidazolidin-1-yl)ethyl)amino)acetonitrile | 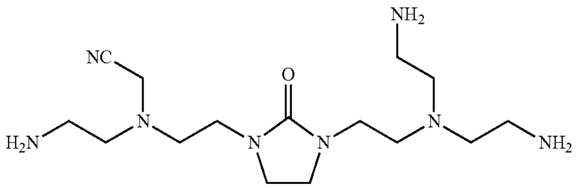 [SMILES: N#CCN(CCN)CCN1CCN(CCN(CCN)CCN)C1=O] |
| U3-T-HEHA | 2-((2-((2-(3-(2-((2-aminoethyl)(2-((cyanomethyl)amino)ethyl)amino)ethyl)-2-oxoimidazolidin-1-yl)ethyl)amino)ethyl)amino)acetonitrile | 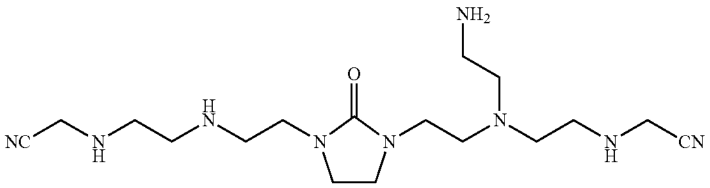 [SMILES: N#CCNCCNCCN1CCN(CCN(CCN)CCNCC#N)C1=O] |
| U3-T-HEHA | 2,2'-((((2-(3-(2-((2-aminoethyl)amino)ethyl)-2-oxoimidazolidin-1-yl)ethyl)azanediyl)bis(ethane-2,1-diyl))bis(azanediyl))diacetonitrile | 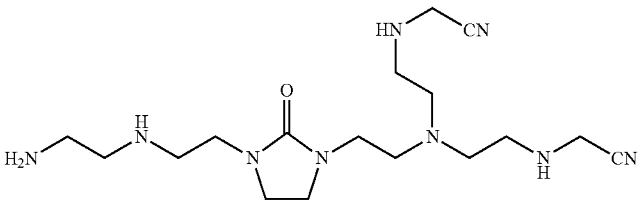 [SMILES: N#CCNCCN(CCNCC#N)CCN1CCN(CCNCCN)C1=O] |
| U3-T-HEHA | 2-((2-aminoethyl)(2-(3-(2-((2-aminoethyl)(2-((cyanomethyl)amino)ethyl)amino)ethyl)-2-oxoimidazolidin-1-yl)ethyl)amino)acetonitrile | 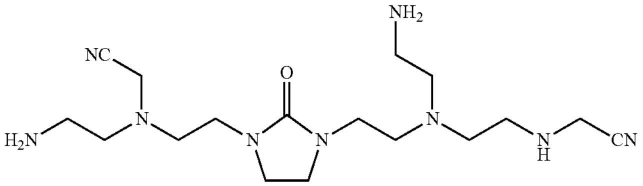 [SMILES: N#CCNCCN(CCN)CCN1CCN(CCN(CC#N)CCN)C1=O] |

-continued

| amine starting materi-al | nitrile product | structure |
|---|---|---|
| U3-T-HEHA | 2,2'-((2-((2-aminoethyl)(2-(3-(2-((2-aminoethyl)amino)ethyl)-2-oxoimidazolidin-1-yl)ethyl)amino)ethyl)azane-diyl)diacetonitrile | 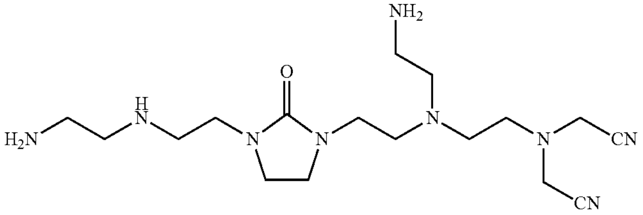 [SMILES: N#CCN(CC#N)CCN(CCN)CCN1CCN(CCNCCN)C1=O] |
| U3-T-HEHA | 2,2'-((2-((2-(3-(2-(bis(2-aminoethyl)amino)ethyl)-2-oxoimidazolidin-1-yl)ethyl)amino)ethyl)azane-diyl)diacetonitrile | 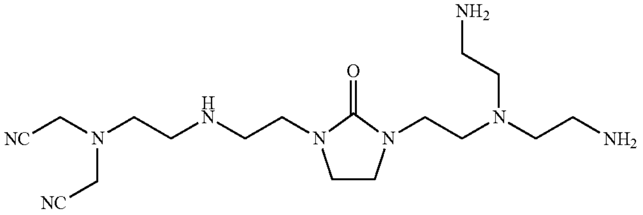 [SMILES: N#CCN(CC#N)CCNCCN1CCN(CCN(CCN)CCN)C1=O] |
| U3-T-HEHA | 2,2'-((((2-(3-(2-((2-((cyanomethyl)amino)eth-yl)amino)ethyl)-2-oxoimdiazolidin-1-yl)ethyl)azanediyl)bis(eth-ane-2,1-diyl))bis(azanediyl))diace-tonitrile | 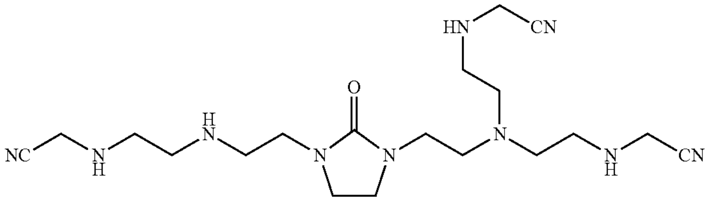 [SMILES: N#CCNCCNCCN1CCN(CCN(CCNCC#N)CCNCC#N)C1=O] |
| U3-T-HEHA | 2-((2-(3-(2-((2-aminoethyl)(2-((cyanomethyl)amino)eth-yl)amino)ethyl)-2-oxoimidazolidin-1-yl)ethyl)(2-((cyanomethyl)amino)eth-yl)amino)acetonitrile | 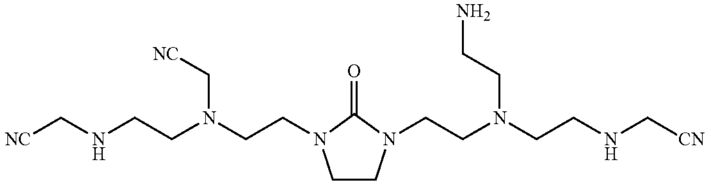 [SMILES: N#CCNCCN(CC#N)CCN1CCN(CCN(CCN)CCNCC#N)C1=O] |
| U3-T-HEHA | 2,2'-((((2-(3-(2-((2-aminoethyl)(cyanomethyl) amino)ethyl)-2-oxoimidazolidin-1-yl)ethyl)azanediyl)bis(eth-ane-2,1-diyl))bis(azanediyl))diace-tonitrile | 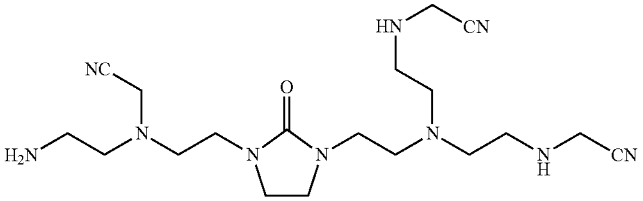 [SMILES: N#CCNCCN(CCNCC#N)CCN1CCN(CCN(CC#N)CCN)C1=O] |
| U3-T-HEHA | 2,2'-((2-((2-(3-(2-((2-aminoethyl)amino)ethyl)-2-oxoimidazolidin-1-yl)ethyl)(2-((cyanomethyl)amino)eth-yl)amino)ethyl)azanediyl) diacetonitrile | 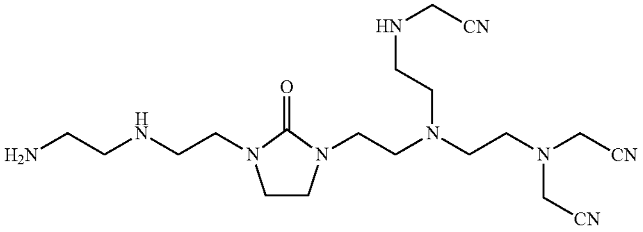 [SMILES: N#CCNCCN(CCN(CC#N)CC#N)CCN1CCN(CCNCCN)C1=O] |
| U3-T-HEHA | 2,2'-((2-((2-aminoethyl)(2-(3-(2-((2-((cyanomethyl)amino)eth-yl)amino)ethyl)-2-oxoimidazolidin-1-yl)ethyl)amino)ethyl)azane-diyl)diacetonitrile | 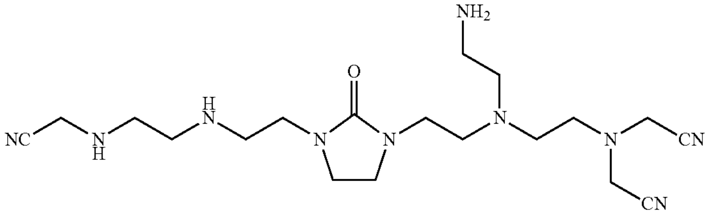 [SMILES: N#CCNCCNCCN1CCN(CCN(CCN)CCN(CC#N)CC#N)C1=O] |

-continued

| amine starting materi-al | nitrile product | structure |
| --- | --- | --- |
| U3-T-HEHA | 2,2'-((2-((2-aminoethyl)(2-(3-(2-((2-aminoethyl)(cyanomethyl) amino)ethyl)-2-oxoimidazolidin-1-yl)ethyl)amino)ethyl)azane-diyl)diacetonitrile | 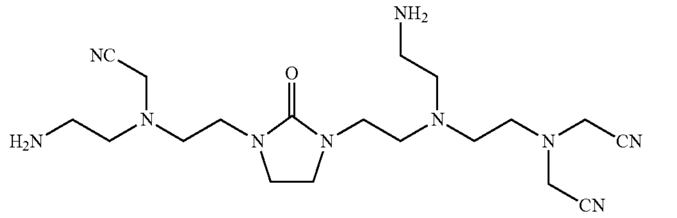 [SMILES: N#CCN(CC#N)CCN(CCN)CCN1CCN(CCN(CC#N)CCN)C1=O] |
| U3-T-HEHA | 2,2'-((2-((2-(3-(2-((2-aminoethyl)(2-((cyanomethyl)amino)eth-yl)amino)ethyl)-2-oxoimidazolidin-1-yl)ethyl)amino)ethyl)azane-diyl)diacetonitrile | 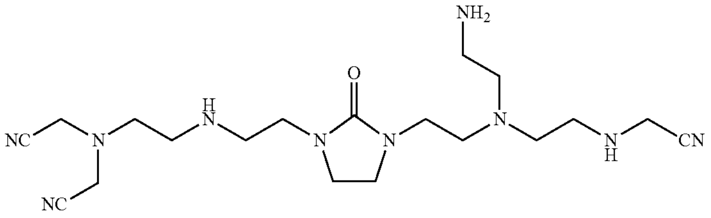 [SMILES: N#CCNCCN(CCN)CCN1CCN(CCNCCN(CC#N)CC#N)C1=O] |
| U3-T-HEHA | 2,2'-((2-((2-(3-(2-(bis(2-aminoethyl)amino)ethyl)-2-oxoimidazolidin-1-yl)ethyl)(cyanomethyl)ami-no)ethyl)azanediyl)diaceto-nitrile | 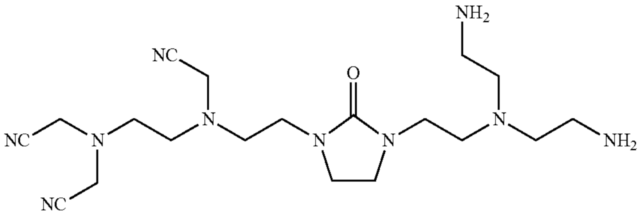 [SMILES: N#CCN(CC#N)CCN(CC#N)CCN1CCN(CCN(CCN)CCN)C1=O] |
| U3-T-HEHA | 2,2'-((((2-(3-(2-((cyanomethyl)(2-((cyanomethyl)amino)eth-yl)amino)ethyl)-2-oxoimidazolidin-1-yl)ethyl)azanediyl)bis(eth-ane-2,1-diyl))bis(azanediyl))diace-tonitrile | 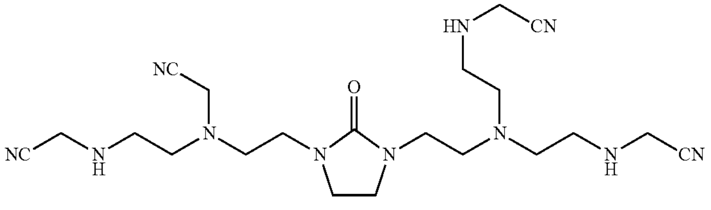 [SMILES: N#CCNCCN(CC#N)CCN1CCN(CCN(CCNCC#N)CCNCC#N)C1=O] |
| U3-T-HEHA | 2,2'-((2-((2-((cyanomethyl)amino)eth-yl)(2-(3-(2-((2-((cyanomethyl)amino)eth-yl)amino)ethyl)-2-oxoimidazolidin-1-yl)ethyl)amino)ethyl)azane-diyl)diacetonitrile | 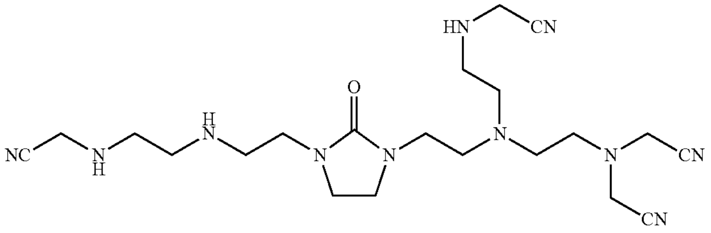 [SMILES: N#CCNCCNCCN1CCN(CCN(CCNCC#N)CCN(CC#N)CC#N)C1=O] |
| U3-T-HEHA | 2,2'-((2-((2-(3-(2-((2-aminoethyl)(cyanomethyl) amino)ethyl)-2-oxoimidazolidin-1-yl)ethyl)(2-((cyanomethyl)amino)eth-yl)amino)ethyl)azanediyl) diacetonitrile | 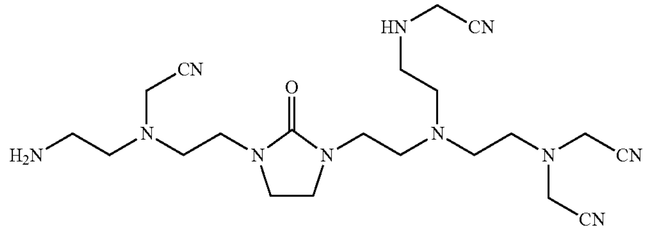 [SMILES: N#CCNCCN(CCN(CC#N)CC#N)CCN1CCN(CCN(CC#N)CCN)C1=O] |

-continued

| amine starting material | nitrile product | structure |
| --- | --- | --- |
| U3-T-HEHA | 2,2',2'',2'''-((((2-(3-(2-((2-aminoethyl)amino)ethyl)-2-oxoimidazolidin-1-yl)ethyl)azanediyl)bis(ethane-2,1-diyl))bis(azanetriyl))tetraacetonitrile | 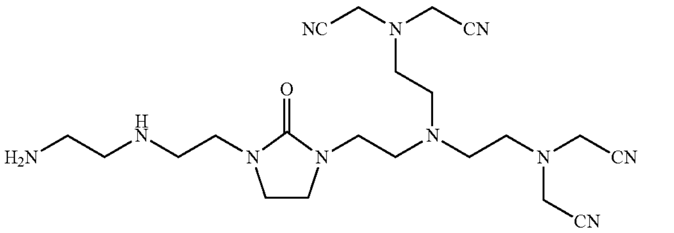 [SMILES: N#CCN(CC#N)CCN(CCN(CC#N)CC#N)CCN1CCN(CCNCCN)C1=O] |
| U3-T-HEHA | 2,2'-((2-((2-(3-(2-(bis(2-((cyanomethyl)amino)ethyl)amino)ethyl)-2-oxoimidazolidin-1-yl)ethyl)amino)ethyl)azanediyl)diacetonitrile | 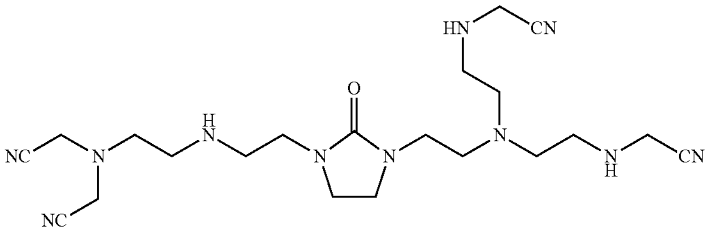 [SMILES: N#CCNCCN(CCNCC#N)CCN1CCN(CCNCCN(CC#N)CC#N)C1=O] |
| U3-T-HEHA | 2,2'-((2-((2-(3-(2-((2-aminoethyl)(2-((cyanomethyl)amino)ethyl)amino)ethyl)-2-oxoimidazolidin-1-yl)ethyl)(cyanomethyl)amino)ethyl)azanediyl)diacetonitrile | 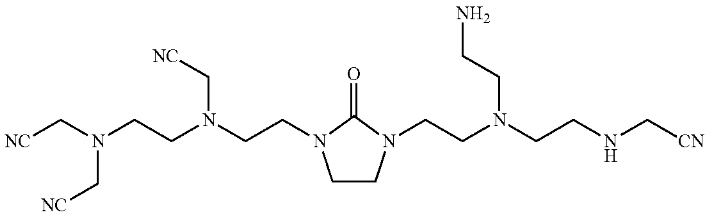 [SMILES: N#CCNCCN(CCN)CCN1CCN(CCN(CC#N)CCN(CC#N)CC#N)C1=O] |
| U3-T-HEHA | 2,2'-((2-((2-(3-(2-(bis(2-((cyanomethyl)amino)ethyl)amino)ethyl)-2-oxoimidazolidin-1-yl)ethyl)(cyanomethyl)amino)ethyl)azanediyl)diacetonitrile | 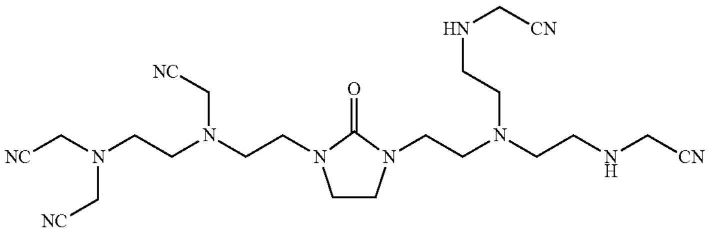 [SMILES: N#CCNCCN(CCNCC#N)CCN1CCN(CCN(CC#N)CCN(CC#N)CC#N)C1=O] |
| U3-T-HEHA | 2,2'-((2-((2-(3-(2-((cyanomethyl)(2-((cyanomethyl)amino)ethyl)amino)ethyl)-2-oxoimidazolidin-1-yl)ethyl)(2-((cyanomethyl)amino)ethyl)amino)ethyl)azanediyl) diacetonitrile | 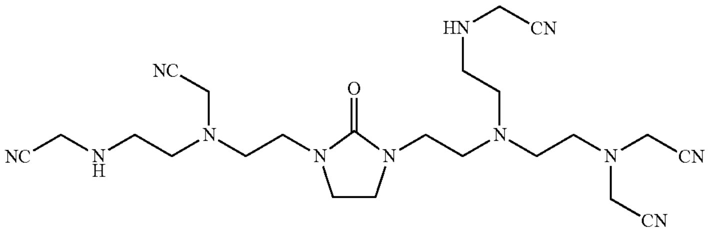 [SMILES: N#CCNCCN(CC#N)CCN1CCN(CCN(CCNCC#N)CCN(CC#N)CC#N)C1=O] |
| U3-T-HEHA | 2,2',2'',2'''-((((2-(3-(2-((2-((cyanomethyl)amino)ethyl)amino)ethyl)-2-oxoimidazolidin-1-yl)ethyl)azanediyl)bis(ethane-2,1-diyl))bis(azanetriyl))tetraacetonitrile | 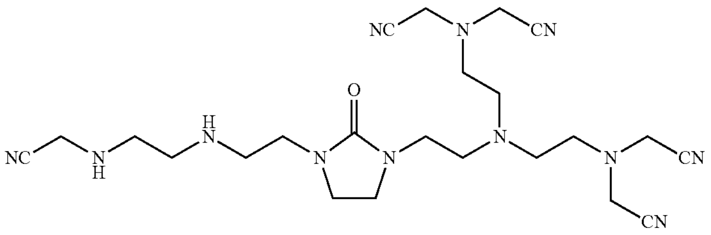 [SMILES: N#CCNCCNCCN1CCN(CCN(CCN(CC#N)CC#N)CCN(CC#N)CC#N)C1=O] |

-continued

| amine starting materi-al | nitrile product | structure |
|---|---|---|
| U3-T-HEHA | 2,2',2'',2'''-((((2-(3-(2-((2-aminoethyl)(cyanomethyl)amino)ethyl)-2-oxoimidazolidin-1-yl)ethyl)azanediyl)bis(ethane-2,1-diyl))bis(azanetriyl))tetraacetonitrile | 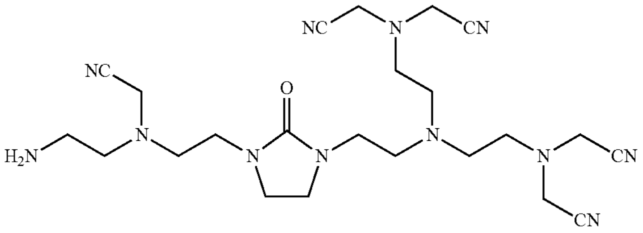 [SMILES: N#CCN(CC#N)CCN(CCN(CC#N)CC#N)CCN1CCN(CCN(CC#N)CCN)C1=O] |
| U3-T-HEHA | 2,2'-((2-((2-(3-(2-((2-(bis(cyanomethyl)amino)ethyl)(2-((cyanomethyl)amino)ethyl)amino)ethyl)-2-oxoimidazolidin-1-yl)ethyl)amino)ethyl)azanediyl)diacetonitrile | 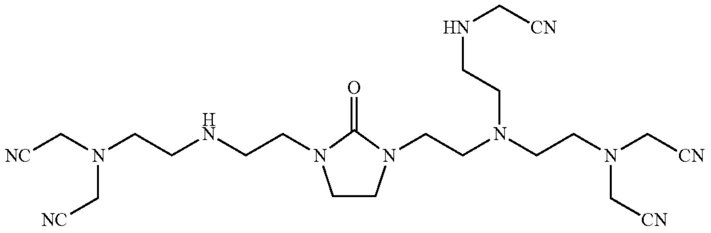 [SMILES: N#CCNCCN(CCN(CC#N)CC#N)CCN1CCN(CCNCCN(CC#N)CC#N)C1=O] |
| U3-T-HEHA | 2,2'-((2-((2-aminoethyl)(2-(3-(2-((2-(bis(cyanomethyl)amino)ethyl)(cyanomethyl)amino)ethyl)-2-oxoimdiazolidin-1-yl)ethyl)amino)ethyl)azanediyl)diacetonitrile | 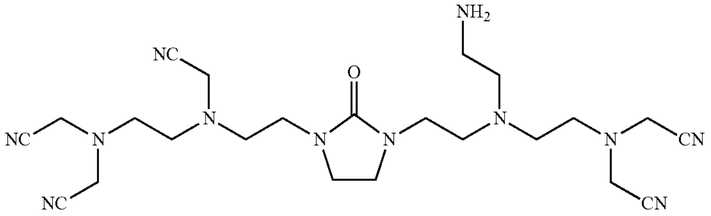 [SMILES: N#CCN(CC#N)CCN(CC#N)CCN1CCN(CCN(CCN)CCN(CC#N)CC#N)C1=O] |
| U3-T-HEHA | 2,2'-((2-((2-(3-(2-((2-(bis(cyanomethyl)amino)ethyl)(2-((cyanomethyl)amino)ethyl)amino)ethyl)-2-oxoimdiazolidin-1-yl)ethyl)(cyanomethyl)amino)ethyl)azanediyl)diacetonitrile | 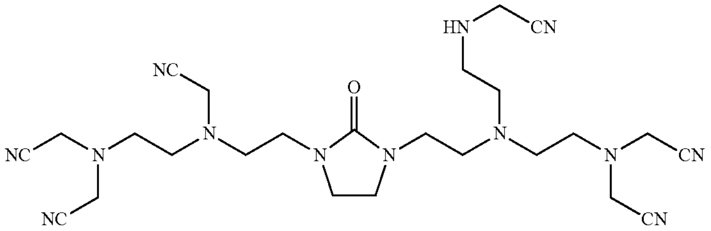 [SMILES: N#CCNCCN(CCN(CC#N)CC#N)CCN1CCN(CCN(CC#N)CCN(CC#N)CC#N)C1=O] |
| U3-T-HEHA | 2,2',2'',2'''-((((2-(3-(2-((2-(bis(cyanomethyl)amino)ethyl)amino)ethyl)-2-oxoimidazolidin-1-yl)ethyl)azanediyl)bis(ethane-2,1-diyl))bis(azanetrieyl))tetraacetonitrile | 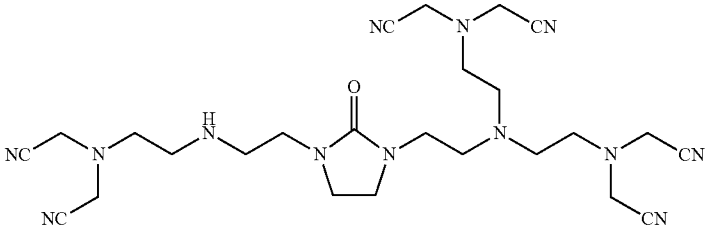 [SMILES: N#CCN(CC#N)CCNCCN1CCN(CCN(CCN(CC#N)CC#N)CCN(CC#N)CC#N)C1=O] |
| U3-T-HEHA | 2,2',2'',2'''-((((2-(3-(2-((cyanomethyl)(2-((cyanomethyl)amino)ethyl)amino)ethyl)-2-oxoimidazolidin-1-yl)ethyl)azanediyl)bis(ethane-2,1-diyl))bis(azanetriyl))tetraacetonitrile | 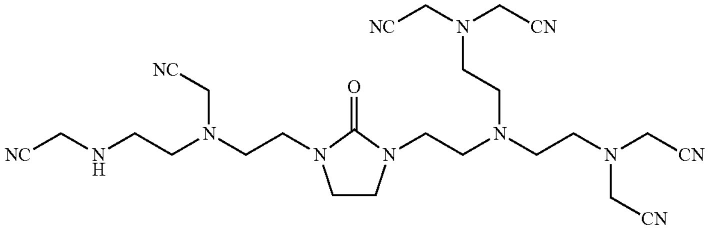 [SMILES: N#CCNCCN(CC#N)CCN1CCN(CCN(CCN(CC#N)CC#N)CCN(CC#N)CC#N)C1=O] |

-continued

| amine starting materi-al | nitrile product | structure |
|---|---|---|
| U3-T-HEHA | 2,2',2'',2'''-((((2-(3-(2-((2-(bis(cyanomethyl)amino)ethyl)(cyanomethyl)amino)ethyl)-2-oxoimidazolidin-1-yl)ethyl)azanediyl)bis(ethane-2,1-diyl))bis(azanetrieyl))tetraacetonitrile | 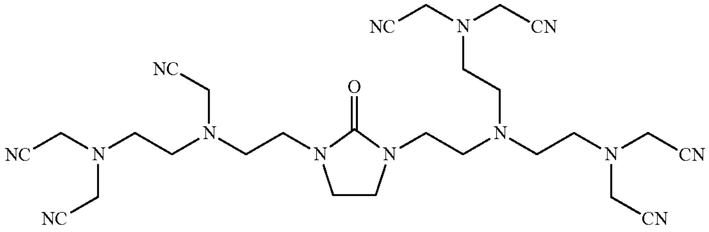 [SMILES: N#CCN(CC#N)CCN(CC#N)CCN1CCN(CCN(CCN(CC#N)CC#N)CCN(CC#N)CC#N)C1=O] |
| U1P3-PEHA | 2-((2-((2-(4-(2-(2-oxoimidazolidin-1-yl)ethyl)piperazin-1-yl)ethyl)amino)ethyl)amino)acetonitrile, U1P3-PEHA monoacetonitrile) | 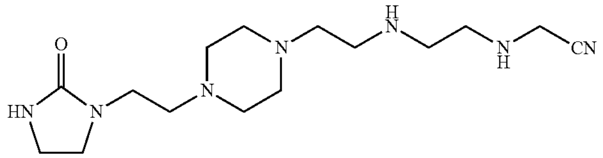 [SMILES: N#CCNCCNCCN1CCN(CCN2CCNC2=O)CC1] |
| U1P3-PEHA | 2-((2-aminoethyl)(2-(4-(2-(2-oxoimidazolidin-1-yl)ethyl)piperazin-1-yl)ethyl)amino)acetonitrile | 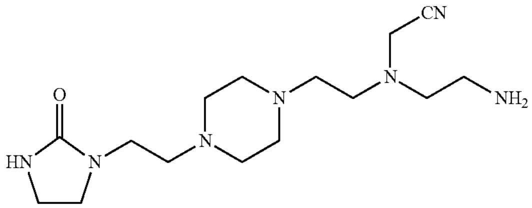 [SMILES: N#CCN(CCN)CCN1CCN(CCN2CCNC2=O)CC1] |
| U1P3-PEHA | 2-((2-((cyanomethyl)(2-(4-(2-(2-oxoimidazolidin-1-yl)ethyl)piperazin-1-yl)ethyl)amino)ethyl)amino)acetonitrile | 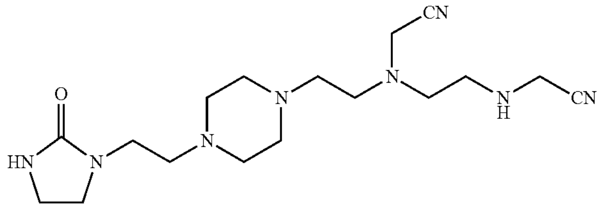 [SMILES: N#CCNCCN(CC#N)CCN1CCN(CCN2CCNC2=O)CC1] |
| U1P3-PEHA | 2,2'-((2-((2-(4-(2-(2-oxoimidazolidin-1-yl)ethyl)piperazin-1-yl)ethyl)amino)ethyl)azanediyl)diacetonitrile | 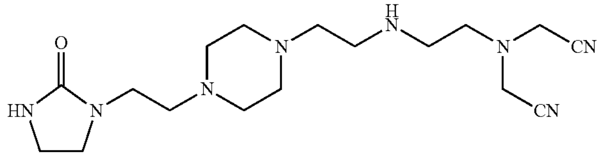 [SMILES: N#CCN(CC#N)CCNCCN1CCN(CCN2CCNC2=O)CC1] |
| U1P3-PEHA | 2,2'-((2-((cyanomethyl)(2-(4-(2-(2-oxoimidazolidin-1-yl)ethyl)piperazin-1-yl)ethyl)amino)ethyl)azanediyl)diacetonitrile | 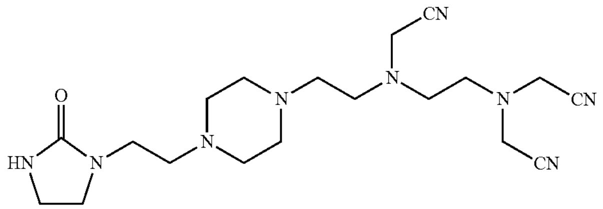 [SMILES: N#CCN(CC#N)CCN(CC#N)CCN1CCN(CCN2CCNC2=O)CC1] |
| U1P3-T-HEHA | 2-((2-((2-aminoethyl)(2-(4-(2-(2-oxoimidazolidin-1-yl)ethyl)piperazin-1-yl)ethyl)amino)ethyl)amino)acetonitrile, | 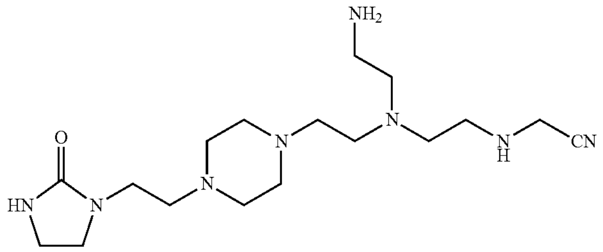 [SMILES: N#CCNCCN(CCN)CCN1CCN(CCN2CCNC2=O)CC1] |

-continued

| amine starting material | nitrile product | structure |
|---|---|---|
| U1P3-T-HEHA | 2,2'-((((2-(4-(2-(2-oxoimidazolidin-1-yl)ethyl)piperazin-1-yl)ethyl)azanediyl)bis(ethane-2,1-diyl))bis(azanediyl))diacetonitrile | 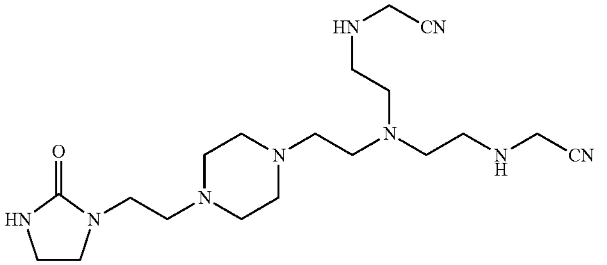 [SMILES: N#CCNCCN(CCNCC#N)CCN1CCN(CCN2CCNC2=O)CC1] |
| U1P3-T-HEHA | 2,2'-((2-((2-((cyanomethyl)amino)ethyl)(2-(4-(2-(2-oxoimidazolidin-1-yl)ethyl)piperazin-1-yl)ethyl)amino)ethyl)azanediyl)diacetonitrile | 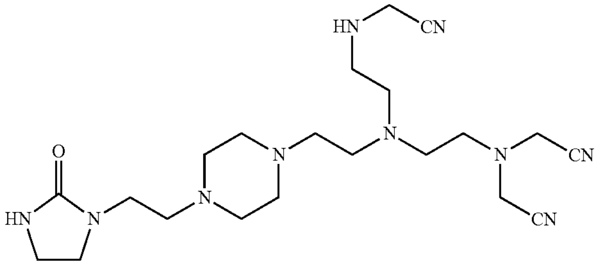 [SMILES: N#CCNCCN(CCN(CC#N)CC#N)CCN1CCN(CCN2CCNC2=O)CC1] |
| U1P3-T-HEHA | 2,2',2'',2'''-((((2-(4-(2-(2-oxoimidazolidin-1-yl)ethyl)piperazin-1-yl)ethyl)azanediyl)bis(ethane-2,1-diyl))bis(azanetrieyl))tetraacetonitrile | 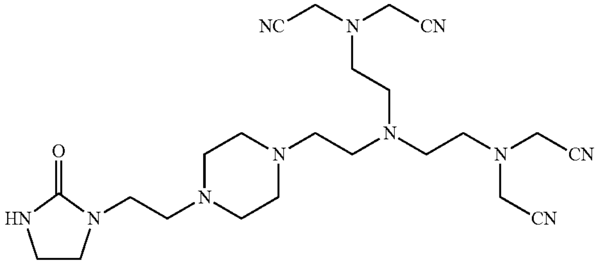 [SMILES: N#CCN(CC#N)CCN(CCN(CC#N)CC#N)CCN1CCN(CCN2CCNC2=O)CC1] |
| U3-T-HEOA | 2-((2-((2-((2-aminoethyl)(2-(3-(2-((2-aminoethyl)amino)ethyl)-2-oxoimidazolidin-1-yl)ethyl)amino)ethyl)amino)ethyl)amino)acetonitrile, | 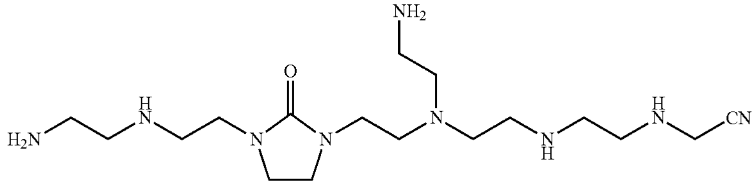 [SMILES: N#CCNCCNCCN(CCN)CCN1CCN(CCNCCN)C1=O] |

In one embodiment, in a next step, the acetonitrile group resulting from the process of the present disclosure is reacted further. For example, in one embodiment, the nitrile unit is hydrogenated to provide an amine group. For example, in another embodiment, the nitrile unit is hydrolyzed to give a terminal amide (under neutral or mild acidic conditions) or carboxylic acid group (under alkaline conditions). For example, in a further embodiment, the nitrile group is reacted with Grignard reagents to form an imine salt which can then be hydrolyzed to yield a ketone.

If so desired, the cyclic urea protective group can be removed from the product obtained by the process as contemplated herein. In one embodiment, this can be done by reaction under alkaline conditions. In that case, if the acetonitrile groups are not yet converted to another group in the formed products, they will under the alkaline conditions also get saponified to carboxylic acid groups. Hence, the removal of the cyclic urea unit and the saponification of the acetonitrile groups to carboxymethyl groups can be done simultaneously. However, if it is desired to react the nitrile group with another chemical to convert it to amine unit, in some embodiments it may be preferred to first perform such reaction before the cyclic urea unit is removed. This will be discussed in more detail below.

The following reaction schemes illustrate possible further reactions, with products derived from U-DETA as starting compounds.

Catalytic Hydrogenation of the Acetonitrile Groups

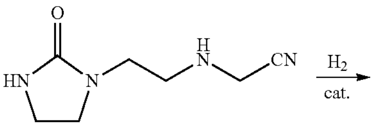

-continued

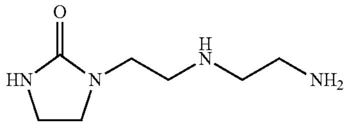

U1-TETA

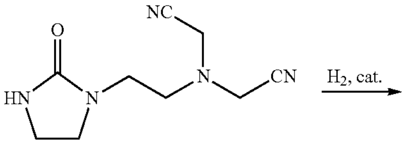

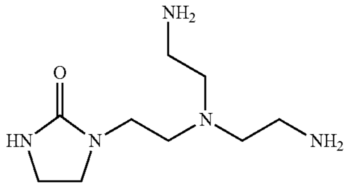

U-T-TEPA

+

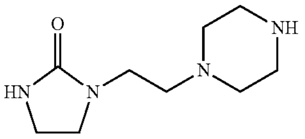

UP-TETA

Saponification of the Acetonitrile Groups

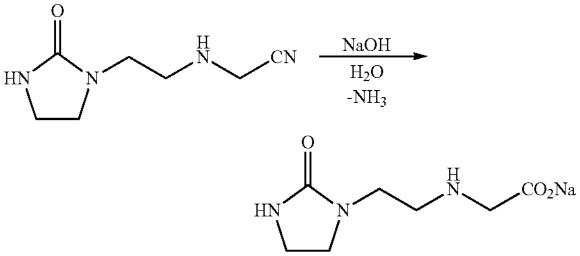

Removing the Cyclic Urea Unit from the Hydrogenated Product

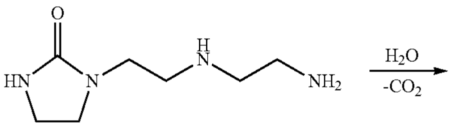

U1-TETA

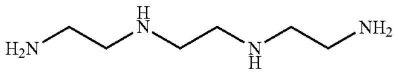

L-TETA

-continued

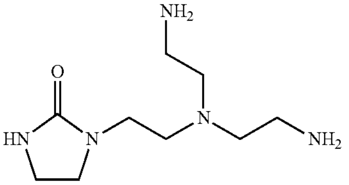

U-T-TEPA

+

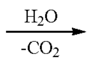

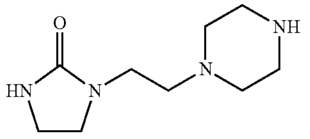

UP-TETA

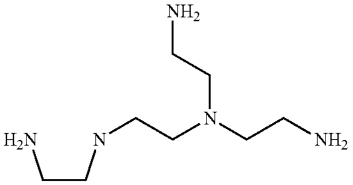

T-TEPA

+

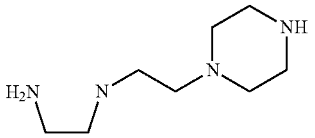

P1-TETA

In one embodiment, the nitrile product of the process as contemplated herein is subjected to a catalytic hydrogenation step, in which the nitrile compound is reacted with hydrogen to convert the nitrile into the corresponding amine. Catalytic hydrogenation of the acetonitrile products of the present disclosure is preferably carried out using a hydrogenation catalyst, e.g. Raney-Cobalt or Raney-Nickel, supported catalysts containing an element of Group 8 of the periodic table, e.g. Fe, Co, Ni, Cu, Ru, Rh, Pd, Os, Ir, Pt, preferably Fe, Co, Ni, Ru or Rh, particularly Co or Ni. The catalyst may be supported on an inorganic oxidic carrier, e.g. based on alumina, silica, titania, zirconia, or combinations thereof, or on a porous carbon carrier.

The reaction may be carried out at temperatures from 40 to 150° C., preferably from 70 to 140° C., in particular from 80 to 140° C. and a pressures from 5 to 300 bar, preferably 30 to 250 bar, in particular 40 to 160 bar. Catalytic hydrogenation of acetonitrile products is known in the art, and requires no further elucidation here.

The hydrogenation process results in the formation of alkyleneamine compounds, which, as compared to the starting compound of the process as contemplated herein, have gained additional ethyleneamine groups. Therewith, the process as contemplated herein makes it possible to obtain chain-extended alkyleneamine compounds.

The following table shows examples of the starting material, the nitrile, and the resulting amine product:

| amine starting material | nitrile product | amine product after hydrogenation reaction |
|---|---|---|
| U-DETA | U-DETA monoacetonitrile | U1-TETA |
| U-DETA | U-DETA diacetonitrile | U1-T-TEPA + UP-TETA |
| U1-TETA | ((2-(2-oxoimidazolidin-1-yl)ethyl)amino)acetonitrile U1-TETA monoacetonitrile | U1-TEPA + UP-TETA |
| U2-TETA | 2,2'-(((2-oxoimidazolidine-1,3-diyl)bis(ethane-2,1-diyl))bis(azanediyl))diacetonitrile U2-TETA monoacetonitrile | U2-TEPA |
| UP-TETA | UP-TETA monoacetonitrile | U1P3-TEPA |
| DU1,3-TEPA | DU1,3-TEPA monoacetonitrile | DU1,3-PEHA |
| DU-1,3-TEPA | DU1,3-TEPA diacetonitrile | DU1,3-T-HEHA + DU1,3P5-PEHA |
| DU1,4-TEPA | DU1,4-TEPA monoacetonitrile | DU1,4-T-PEHA |
| U1P3-TEPA | U1P3-TEPA monoacetonitrile | U1P3-PEHA |
| U1P3-TEPA | U1P3-TEPA diacetonitrile | U1P3-T-HEHA + U1DP3,5-PEHA |
| U1P4-TEPA | U1P4-TEPA monoacetonitrile | U1P4-T-PEHA |

In another embodiment, the nitrile product of the process as contemplated herein is subjected to a saponification step in which the nitrile compound is reacted with a base to form a carboxylic acid salt. This reaction can be carried out subsequent to nitrile formation, but also simultaneously with nitrile formation, if the nitrile formation is carried out using an inorganic cyanide salt as discussed above.

If the saponification of the acetonitrile products is carried out as a separate step, it is preferably done by adding a base, such as an aqueous solution of sodium hydroxide or potassium hydroxide. In a further preferred embodiment the base is used in 0.7 to 1.5 molar equivalent per acetonitrile group. The use of KOH or NaOH as base is preferred, as is the use of an aqueous medium. Saponification processes are known in the art and require no further elucidation here.

The product from the saponification step is a salt of a carboxylic acid.

The following table lists a number of preferred starting material-nitrile intermediate-saponified product combinations:

| amine starting material | nitrile product | saponified product |
|---|---|---|
| U-DETA | U-DETA monoacetonitrile | Monocarboxymethyl U-DETA |
| U-DETA | U-DETA diacetonitrile | Dicarboxymethyl U-DETA |
| U1-TETA | ((2-(2-oxoimidazolidin-1-yl)ethyl)amino)acetonitrile U1-TETA monoacetonitrile | Monocarboxymethyl U1-TETA |
| U2-TETA | 2,2'-(((2-oxoimidazolidine-1,3-diyl)bis(ethane-2,1-diyl))bis(azanediyl))diacetonitrile U2-TETA monoacetonitrile | Monocarboxymethyl U2-TETA |
| UP-TETA | UP-TETA monoacetonitrile | Monocarboxymethyl UP-TETA |
| DU1,3-TEPA | DU1,3-TEPA monoacetonitrile | Monocarboxymethyl DU1,3-TEPA |
| DU-1,3-TEPA | DU1,3-TEPA diacetonitrile | Dicarboxymethyl DU1,3-TEPA |
| DU1,4-TEPA | DU1,4-TEPA monoacetonitrile | Monocarboxymethyl DU1,4-TEPA |
| U1P3-TEPA | U1P3-TEPA monoacetonitrile | Monocarboxymethyl U1P3-TEPA |
| U1P3-TEPA | U1P3-TEPA diacetonitrile | Dicarboxymethyl U1P3-TEPA |
| U1P4-TEPA | U1P4-TEPA monoacetonitrile | Monocarboxymethyl U1P4-TEPA |

In one embodiment, the nitrile group is reacted with a Grignard reagent to form an imine salt which can then be hydrolyzed to yield a ketone.

A Grignard reagent is a compound of the formula R—Mg—X, where X is a halogen and R is an organic group, normally an alkyl or aryl. X is generally selected from Cl, Br and I. Examples of suitable R grounds include C1-C10 alkyl and C5-C10 aryl, alkylaryl, and arylalkyl. R is, e.g., selected from methyl, ethyl, propyl, and phenyl. Examples include methylmagnesium chloride and phenylmagnesium bromide. The reaction with the Grignard reagents results in the formation of imine compounds. By reaction with water, preferably under acidic conditions, the imine can be converted into a ketone. It is important that water is added only after the imine is formed, because the presence of water will lead to destruction of the Grignard reagent.

Reaction of nitrile groups with a Grignard reagent to form an imine followed by hydrolysis to form a ketone is known in the art and requires no further elucidation here.

In a further embodiment, aminonitrile compounds obtained by the process of the present disclosure are subjected to a hydrolysis step to manufacture the corresponding amides. This reaction can be carried out in a solvent, in particular a protonic solvent, preferably in water, using an acidic catalyst. Suitable catalysts include conventional acidic catalysts such as inorganic acids, e.g., sulphuric acid, nitric acid, hydrochloric acid, and hydrobromic acid, and organic acid such as formic acid, citric acid, acetic acid, trifluoroacetic acid, and combinations thereof.

Hydrolysis of aminonitrile compounds to form the corresponding amide compounds is known in the art, and requires no further elucidation here.

The following table lists a number of preferred starting materials, the corresponding nitrile intermediates and amide product combinations:

| amine starting material | nitrile product | amide product |
|---|---|---|
| U-DETA | U-DETA monoacetonitrile | Monocarboxyamide U-DETA |
| U-DETA | U-DETA diacetonitrile | Dicarboxyamide U-DETA |
| U1-TETA | ((2-(2-oxoimidazolidin-1-yl)ethyl)amino)acetonitrile U1-TETA monoacetonitrile | Monocarboxyamide U1-TETA |
| U2-TETA | 2,2'-(((2-oxoimidazolidine-1,3-diyl)bis(ethane-2,1-diyl))bis(azanediyl))diacetonitrile U2-TETA monoacetonitrile | Monocarboxyamide U2-TETA |
| UP-TETA | UP-TETA monoacetonitrile | Monocarboxyamide UP-TETA |
| DU1,3-TEPA | DU1,3-TEPA monoacetonitrile | Monocarboxyamide DU1,3-TEPA |
| DU-1,3-TEPA | DU1,3-TEPA diacetonitrile | Dicarboxyamide DU1,3-TEPA |
| DU1,4-TEPA | DU1,4-TEPA monoacetonitrile | Monocarboxyamide DU1,4-TEPA |

-continued

| amine starting material | nitrile product | amide product |
|---|---|---|
| U1P3-TEPA | U1P3-TEPA monoacetonitrile | Monocarboxyamide U1P3-TEPA |
| U1P3-TEPA | U1P3-TEPA diacetonitrile | Dicarboxyamide U1P3-TEPA |
| U1P4-TEPA | U1P4-TEPA monoacetonitrile | Monocarboxyamide U1P4-TEPA |

In one embodiment, the cyclic urea protective group is removed from the product obtained by the process as contemplated herein. Depending on the reaction conditions in the urea removal step, this can be done on the nitrile product, or on the products from the further reactions discussed above. It is within the scope of the skilled person to select the appropriate reaction sequence, taking the reactivity of the end groups and the reaction conditions prevailing in the urea removal step into account.

In the present specification, compounds containing a cyclic urea protective group may also be indicated as U-compounds or U-alkyleneamine compounds, to reflect that the removal of the cyclic urea protective group results in the liberation of the two amine groups previously protected by incorporation in the cyclic urea group. This process may also be indicated as a CO2 elimination step. It can be carried out in different ways.

In one embodiment, a U-alkyleneamine compound is reacted in the liquid phase with water to form the corresponding alkyleneamine compound, under removal of CO2. The reaction with water generally takes place at a temperature of at least 150° C. If the reaction temperature is below 150° C., the U-compound will not react to a significant extent. It is preferred for the reaction to be carried out at a temperature of at least 180° C., in particular at least 200° C., more in particular at least 230° C., or even at least 250° C. Preferably the temperature during this step does not exceed 400° C., in particular at most 350° C., more in particular at most 320° C.

The pressure during the process is not critical, as long as the reaction medium is in the liquid phase. As a general range, a value of 0.5 to 100 bar may be mentioned, depending on the desired temperature. It is preferred for the CO2 removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

The amount of water depends on the desired degree of conversion and on the process conditions. In general, the amount of water is at least 0.1 mole water per mole urea moiety in the feedstock. Higher amounts are often used, e.g., at least 0.1 mole water per mole urea moiety, in particular at least 0.5 mole water per mole urea moiety. The maximum is not critical for the process as contemplated herein, but too large amounts of water will lead to unnecessarily large equipment being required. As a general maximum an amount of at most 500 mol water per mole cyclic ethylene urea moiety may be mentioned, in particular at most 300 mole, more in particular at most 200 mol, in some embodiments at most 100 mol, or at most 50 mol.

It is preferred to carry out CO2 removal during the reaction, e.g., by venting the reaction vessel, and preferably by the provision of a stripping gas such as nitrogen or steam. In one embodiment the U-alkyleneamine compound is reacted in the liquid phase with water in an amount of 0.1-20 mole water per mole urea moiety, at a temperature of at least 230° C., with removal of CO2. It has been found that the use of a low amount of water in combination with a relatively high temperature and CO2 removal results in an efficient process which good conversion and low formation of side products.

In one embodiment, the U-alkyleneamine compound is reacted with an alkyleneamine that is capable of picking up a carbonyl moiety, resulting in the conversion of the U-alkyleneamine compound into its corresponding alkyleneamine compound and simultaneous conversion of the alkyleneamine that is capable of picking up a carbonyl moiety into a U-alkyleneamine. This process may be described as a carbonyl transfer reaction.

In a further embodiment, the U-alkyleneamine compound is reacted with a strong base, i.e. a base with a pKb of less than 1, to form the corresponding alkyleneamine compound and a carbonate salt. In this embodiment, the use of a strong inorganic base is considered preferred. In one embodiment, the strong inorganic base is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be considered particularly preferred. Other strong inorganic bases may also be used, such as ammonium hydroxide. As will be evident to the skilled person, mixtures of various inorganic bases can be used. Compounds comprising a base in addition to other components can also be used, as can be compounds which will be converted into inorganic bases in the reaction medium. The molar amount of base can be calculated with respect to the molar amount of alkyleneurea moieties that are to be converted. A value of at least 0.2:1 may be mentioned. If it is desired to obtain full conversion of the alkyleneurea moieties into the corresponding alkyleneamine compound, the use of larger amounts may be preferred, e.g., in a molar ratio of at least 1:1, in particular at least 1.5:1. It may be preferred to use larger amounts to increase the reaction rate, e.g., a molar ratio of at least 2:1, in particular at least 2.5:1. As large amounts of base do not contribute to further conversion but will lead to additional costs, it is preferred for the molar ratio of the base to the molar amount of alkyleneurea be at most 20:1, in particular at most 15:1, more in particular at most 10:1. It has been found that even lower amounts of inorganic base can suffice. More in particular, it has been found that good results can be obtained at a molar ratio of base to alkyleneurea moieties of at most 7.5:1, in particular at most 6.5:1, even more in particular at most 5.5:1. It has been found that the use of a molar ratio of at most 5.5:1 results in full conversion of the alkyleneurea moieties and high yield of the resulting alkyleneamine compounds. It may be preferred to use even less base per mole of alkyleneurea moiety, e.g., in a molar ratio of at most 5:1, in particular at most 4:1, more in particular at most 3:1.

The treatment with base can, for example, be carried out by contacting the material to be treated with a concentrated aqueous solution of the inorganic base. Depending on the nature of the base and the further composition of the reaction mixture, it may also be possible to add the base in solid form and dissolve it in the reaction medium. As will be clear to the skilled person, the aim is to bring the base in a dissolved state, so that the hydroxy groups can react with the CO2 adduct, while avoiding unnecessary dilution of the reaction medium. The reaction can be carried out at a temperature between room temperature and 400° C. The temperature and pressure should be selected such that the reaction mixture is in the liquid phase. Higher temperatures are advantageous because they lead to decreased reaction times. It may be preferred to carry out the reaction at a temperature of at least 100° C., in particular at least 140° C., in particular at least 170° C. On the other hand, higher temperatures may lead to the undesired formation of side products. It may therefore be preferred to carry out the reaction at a temperature of at most 350° C., in particular at most 290° C.

Depending on the reaction temperature, the reaction time can vary within wide ranges, e.g., between 15 minutes and 24 hours. It may be preferred for the reaction time to vary between 1 hour and 12 hours, in particular between 1 hour and 6 hours. When using lower amounts of base, longer reaction times may be required to obtain the desired degree of conversion.

Upon completion of the reaction, a reaction mixture will be obtained which contains ethyleneamine compounds and a carbonate salt of the inorganic base. The salt can be removed by methods known in the art, e.g., by filtration where the salt is in solid form or more in general by phase separation.

Combinations of the various CO2 elimination steps are also possible, e.g., a combination of a treatment with water with CO2 removal, followed by a treatment with base, optionally with an intermediate product removal step.

It will be clear to the skilled person that various preferred embodiments described herein can be combined, unless they are mutually exclusive.

The present disclosure is illustrated by the following examples, without being limited thereto or thereby.

EXAMPLES

Example 1 Chain Elongation of U-DETA to U-DETA Monoacetonitrile Followed by Saponification and Removal of the Cyclic Urea Group

Example 1A: Monocyanomethyl-U-DETA Synthesis by Reaction of U-DETA with Glycolonitrile A solution of U-DETA (68.5 g, 0.5 mol) in water (109 g) and a 58.8% glycolonitrile solution (47.6 g, 0.5 mol) were simultaneously charged into a 1 L reactor containing water (101 g) at 20° C. Glycolonitrile was dosed slightly faster. The dosing temperature was 18° C. The dosing time was 35 minutes. The reaction mixture was kept at RT for 18 h. NMR analysis showed full conversion into the product.

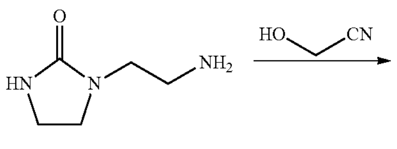

U-DETA

-continued

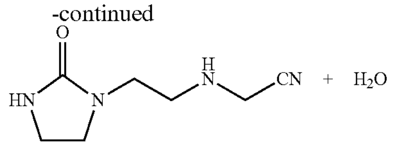

Example 1B: Monocarboxymethyl-U-DETA Synthesis by Saponification of Monocyanomethyl-U-DETA The solution monocyanomethyl-U-DETA (304 g) prepared in the 1 L reactor as described above was added to a mixture of 50% NaOH (44.7 g) and water (128 g) in a stainless steel reactor at 20° C. After stirring for 1 h, the reactor temperature was raised stepwise to the boiling point (104° C.) and was kept at this temperature for 3h with ammonia-water mixture being distilled off. According to NMR analysis full hydrolysis into the product occurred.

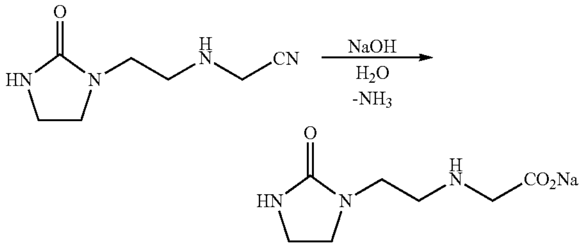

Example 1C: 1-(Carboxymethyl)-Diethylenetriamine Synthesis by Removal of the Cyclic Urea Group from Monocarboxymethyl-U-DETA Hydrolysis experiments were performed using a 50 ml Parr bomb. A 50% NaOH solution was added to the reaction mixture containing monocarboxymethyl-U-DETA sodium salt obtained as described in example 1B above. Incomplete conversion occurred with ca. 2 equivalents of NaOH at 180° C. in 20 h according to NMR analysis. When one extra equivalent of NaOH was added, full hydrolysis occurred at 180° C. in 18 h.

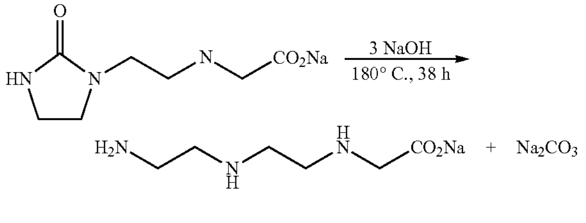

Example 2 Chain Elongation of U-DETA to U-DETA Diacetonitrile Followed by Saponification

Example 2A: Dicyanomethyl-U-DETA Synthesis by Reaction of U-DETA with Formaldehyde and HCN Concentrated sulfuric acid (3 g) was added to a solution of U-DETA (68.5 g, 94.5% purity, 0.5 mol) in water (293 g) in a 1 liter double walled reactor equipped with heating/ cooling bath, and a stirrer to lower pH from 11.7 to 9.5. A 44.2% formaldehyde solution (34 g, 0.5 mol) was added to the obtained solution, which resulted in a further drop of pH to 5.5. This was followed by simultaneous addition of a 44.2% formaldehyde solution (36 g, 0.5 moles) and hydrogen cyanide (27 g, 1 mol) over a period of 90 min. In about 75 min a precipitate was formed and water (100 g) was added to improve the stirrability. After stirring for 1 h the product was discharged from the reactor, which required a significant amount of rinsing water. The product was filtered off and dried.

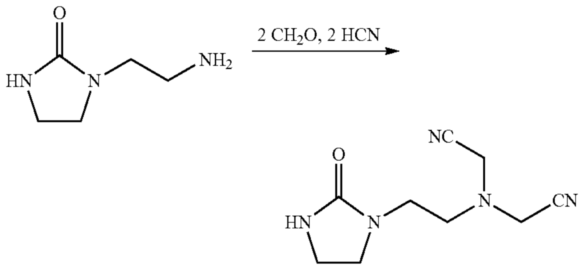

Example 2B: Dicarboxymethyl-UDETA Synthesis by Saponification of Dicyanomethyl-U-DETA The dried dicyanomethyl-U-DETA (70.4 g) prepared as described above was added to a stirred mixture of water (400 g) and 50% NaOH (57 g, 0.6 mol) at 35° C. The mixture was stirred at 35° C. overnight to give a clear solution. The reactor temperature was gradually raised to 105° C. and kept at this temperature for 2 h with ammonia-water mixture being distilled off. Water was added to maintain the temperature at 105° C. A yellow solution (260 g) containing 31.6% (NMR analysis) disodium salt of dicarboxymethyl-U-DETA was obtained, which corresponds to 57% yield based on starting UDETA.

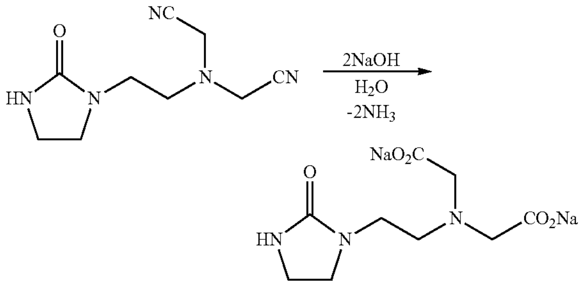

Example 3: Chain Elongation of U-DETA to U-DETA Diacetate Salt via the Reaction of U-DETA with Formaldehyde and an alkali metal cyanide

Example 3A: Dicarboxymethyl-U-DETA Synthesis Through the Reaction of U-DETA with Formaldehyde and an Alkali Metal Cyanide A 30% solution of sodium cyanide was dosed to a 1 L stainless steel reactor containing water (250 g), U-DETA (90.3 g, 94%, 0.7 moles) and 50% NaOH (17 g, 0.2 mol) at 98° C. In 2 minutes after the start of the NaCN dosing, simultaneous dosing of a 44% formaldehyde solution was started. The dosing speed of the NaCN solution was 3.18 g/min for the first 33 minutes, 1.25 g for the next 49 minutes and 1.01 g/min for the remaining time. The total amount of NaCN solution dosed was 230 g. The dosing speed of the formaldehyde solution was 1.31, 0.51 and 0.42 g/min, respectively. The total amount of formaldehyde solution dosed was 97 g. Dosing of formaldehyde was stopped when the amount of free cyanide was below 100 ppm. The reaction mixture was additionally boiled 1 h while removing ammonia-water mixture and adding water to prevent temperature rising above 104° C. After cooling 576.5 g of the reaction solution containing 30.3% (NMR analysis) disodium salt of dicarboxymethyl-U-DETA was discharged from the reactor, which corresponds to 86% yield based on U-DETA.

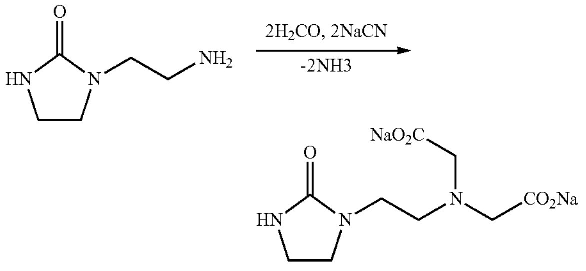

Example 3B 1,1-bis(Carboxymethyl)-Diethylenetriamine Formation by Removal of the Urea Group A 50% NaOH solution (3.5 equivalents) was added to the reaction mixture resulting from the Singer process, which contained dicarboxymethyl-U-DETA sodium salt and the mixture was heated at 180° C. for 40 h. According to NMR analysis, high conversion to the product was obtained.

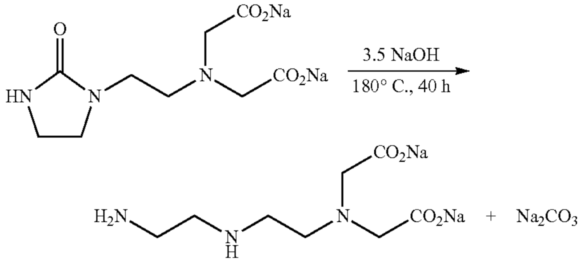

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for manufacturing a nitrile compound through chain elongation of an alkylene amine compound comprising three or more amine units in which at least two amine units are protected by a cyclic urea unit and at least one amine unit is not protected, by reacting the at least one amine unit that is not protected with glycolonitrile or with the combination of formaldehyde and a cyanide compound chosen from HCN and inorganic cyanide salts, to add at least one acetonitrile group to the at least one amine unit that is not protected.

2. The process according to claim 1 wherein the at least one amine unit that is not protected is reacted with glycolonitrile.

3. The process according to claim 1 wherein the at least one amine unit that is not protected is reacted with the combination of formaldehyde and a cyanide compound chosen from HCN and inorganic cyanide salts.

4. The process according to claim 3, wherein the cyanide compound is HCN.

5. The process according to claim 3, wherein the cyanide compound is an inorganic cyanide salt.

6. The process according to claim 5, wherein the reaction is carried out in the presence of an acid.

7. The process according to claim 5, wherein the reaction is carried out in the presence of a base such that the nitrile group is reacted to form a carboxylate.

8. The process of claim 1 wherein the product comprising the at least one acetonitrile group is subjected to a further reaction step which is a hydrogenation step in the presence of hydrogen and a catalyst in which the nitrile group is at least partially converted to an amine group.

9. The process of claim 1 wherein the product comprising the at least one acetonitrile group is subjected to a further reaction step which is a saponification step in the presence of an aqueous base to a carboxylate group.

10. The process according to claim 1, wherein the product comprising the at least one acetonitrile group is subjected to a further reaction step which is a reaction with a Grignard reagent to form an imine salt which is then hydrolyzed to yield a ketone.

11. The process according to claim 1, wherein the product comprising the at least one acetonitrile group is subsequently subjected to a further reaction step which is a hydrolysis step in the presence of an acidic catalyst to form the corresponding amide.

12. The process according to claim 1, in which the alkylene amine compound comprising three or more amine units in which at least two amine units are protected by a cyclic urea unit and at least one amine unit is not protected is chosen from:

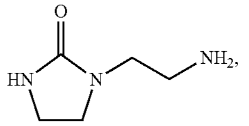

U-DETA

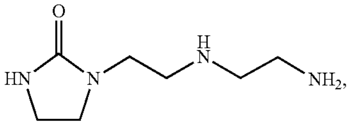

U1-TETA

-continued

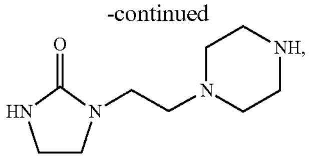

UP-TETA

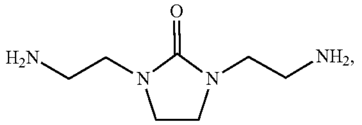

U2-TETA

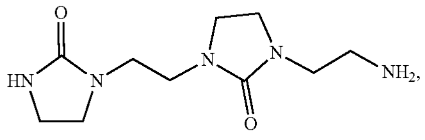

DU1, 3-TEPA

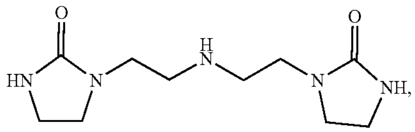

DU1, 4-TEPA

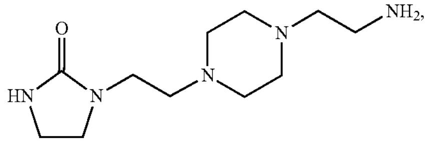

and

U1P3-TEPA

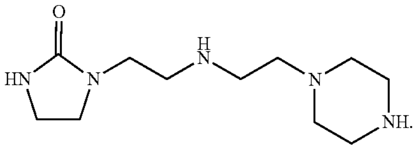

U1P4-TEPA

13. The process according to claim 1, wherein the cyclic urea unit is removed from the nitrile compound.

14. The process of claim 12 wherein the step of removing the cyclic urea unit comprises one or more of reaction with water in a liquid phase, reaction with an alkyleneamine that is capable of picking up a carbonyl moiety, and or reaction with a strong base.

15. The process according to claim 3, wherein the cyanide compound is chosen from sodium cyanide, potassium cyanide, calcium cyanide, and combinations thereof.

16. A process for manufacturing a nitrile compound through chain elongation of an alkylene amine compound comprising three or more amine units in which at least two amine units are protected by a cyclic urea unit and at least one amine unit is not protected, by reacting the at least one amine unit that is not protected with glycolonitrile with the combination of formaldehyde and a cyanide compound chosen from HCN, sodium cyanide, potassium cyanide, calcium cyanide, and combinations thereof, to add at least one acetonitrile group to the at least one amine unit that is not protected, and wherein the alkylene amine compound comprising three or more amine units in which at least two amine units are protected by a cyclic urea unit and at least one amine unit is not protected is chosen from:

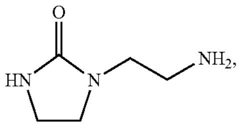

U-DETA

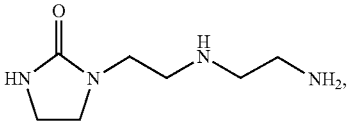

U1-TETA

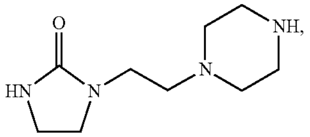

UP-TETA

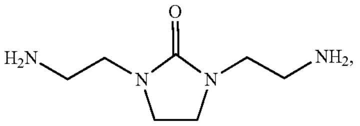

U2-TETA

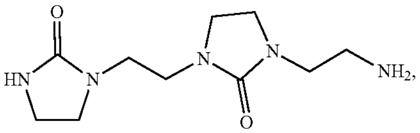

DU1, 3-TEPA

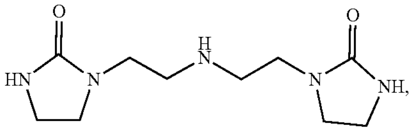

DU1, 4-TEPA

-continued

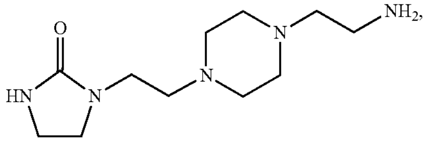

and

U1P3-TEPA

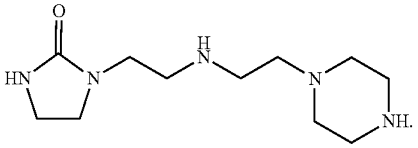

U1P4-TEPA

17. The process according to claim 16, wherein the reaction is carried out in the presence of an acid.

18. The process according to claim 16, wherein the reaction is carried out in the presence of a base such that the nitrile group is reacted to form a carboxylate.

19. The process of claim 16 wherein the product comprising the at least one acetonitrile group is subjected to a further reaction step which is:

a hydrogenation step in the presence of hydrogen and a catalyst in which the nitrile group is at least partially converted to an amine group;

a saponification step in the presence of an aqueous base to form a carboxylate group;

a reaction with a Grignard reagent to form an imine salt which is then hydrolyzed to yield a ketone; or a hydrolysis step in the presence of an acidic catalyst to form the corresponding amide.

* * * * *